US009840546B2

(12) United States Patent
Zhou et al.

(10) Patent No.: US 9,840,546 B2
(45) Date of Patent: Dec. 12, 2017

(54) DOUBLE-STRANDED POLYETHYLENE GLYCOL MODIFIED GROWTH HORMONE, PREPARATION METHOD AND APPLICATION THEREOF

(75) Inventors: Weidong Zhou, Fujian (CN); Xiaojin Liao, Fujian (CN); Li Sun, Fujian (CN); Linzhong Zhang, Fujian (CN); Qingsong Lu, Fujian (CN); Shiye Shen, Fujian (CN); Lishan Yang, Fujian (CN); Defang Zhang, Fujian (CN); Huihuang Lin, Fujian (CN); Ping Zhang, Fujian (CN)

(73) Assignee: Biosteed Gene Expression Tech. Co., Ltd., Fujian (CN)

( * ) Notice: Subject to any disclaimer, the term of this patent is extended or adjusted under 35 U.S.C. 154(b) by 1234 days.

(21) Appl. No.: 12/936,164

(22) PCT Filed: Apr. 3, 2008

(86) PCT No.: PCT/CN2008/000674
§ 371 (c)(1),
(2), (4) Date: Oct. 1, 2010

(87) PCT Pub. No.: WO2009/121210
PCT Pub. Date: Oct. 8, 2009

(65) Prior Publication Data
US 2011/0028388 A1    Feb. 3, 2011

(51) Int. Cl.
| | |
|---|---|
| A61K 38/27 | (2006.01) |
| C07K 14/00 | (2006.01) |
| C07K 14/61 | (2006.01) |
| A61K 47/60 | (2017.01) |

(52) U.S. Cl.
CPC .............. *C07K 14/61* (2013.01); *A61K 38/27* (2013.01); *A61K 47/60* (2017.08)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 5,824,784 A | 10/1998 | Kinstler et al. | |
| 6,342,375 B1 | 1/2002 | Olazaran et al. | |
| 7,026,440 B2 * | 4/2006 | Bentley et al. | 528/407 |
| 8,530,417 B2 * | 9/2013 | Wang et al. | 514/7.9 |
| 2003/0219404 A1 * | 11/2003 | Yamasaki et al. | 424/85.4 |
| 2004/0142870 A1 * | 7/2004 | Finn | 514/12 |
| 2004/0223950 A1 | 11/2004 | Brugger et al. | |
| 2005/0180946 A1 * | 8/2005 | Ji et al. | 424/78.38 |

FOREIGN PATENT DOCUMENTS

| | | |
|---|---|---|
| CN | 1477126 | 2/2004 |
| EP | 0 593 868 | 4/1994 |
| EP | 0 809 996 | 12/1997 |
| EP | 1 496 076 | 1/2005 |
| WO | WO2003/044056 | 5/2003 |
| WO | WO2003/076490 | 9/2003 |
| WO | WO2009/121210 | 10/2009 |

OTHER PUBLICATIONS

Chamow et al., "Modification of CD4 Immunoadhesin with Monomethoxypoly(ethylene glycol) Aldehyde via Reductive Alkylation," Bioconjugate Chemistry. vol. 5, No. 2 pp. 133-140 (1994).
Chen et al., "The Human Growth Hormone Locus: Nucleotide Sequence, Biology and Evolution," Genomics. vol. 4 pp. 479-497 (1989).
Clark et al., "Long-acting Growth Hormones Produced by Conjugation with Polyethylene Glycol," The Journal of Biological Chemistry. vol. 271, No. 36 pp. 21969-21977 (1996).
Delgado et al., "The Uses and Properties of PEG-Linked Proteins," Critical Reviews in Therapeutic Drug Carrier Systems. vol. 9, Nos. 3-4 pp. 249-304 (1992).
DeNoto et al., "Human growth hormone DNA sequence and mRNA structure: possible alternative splicing," Nucleic Acids Research. vol. 9, No. 15 pp. 3719-3730 (1981).
Genbank Accession No. AAA72260.1. Ikehara et al., "Synthesis of a gene for human growth hormone and its expression in *Escherichia coli*," PNAS. vol. 81, No. 19 pp. 5956-5960 (1984).
Genbank Accession No. P01241.2. Roskam, W.G., and Rougeon, F., "Molecular cloning and nucleotide sequence of the human growth hormone structural gene," Nucleic Acids Research. vol. 7, No. 2 pp. 305-320 (1979).
Iglesias et al., "Recombinant Human Growth Hormone Therapy in Malnourished Dialysis Patients: A Randomized Controlled Study," American Journal of Kidney Diseases. vol. 32, No. 3 pp. 454-463 (1998).
Inada et al., "Polyethylene Glycol(PEG)-Protein Conjugates: Application to Biomedical and Biotechnological Processes," Journal of Bioactive and Compatible Polymers. vol. 5 p. 343 (1990).
Inoue et al., "A highly enhanced thrombopoietic activity by monomethoxy polyethylene glycol-modified recombinant human interleukin-6," Journal of Laboratory and Clinical Medicine. vol. 124 p. 529 (1994).
International Preliminary Report on Patentability (Chapter I of the Patent Cooperation Treaty) corresponding to International Patent Application No. PCT/CN2008/000674 dated Oct. 5, 2010.
International Search Report corresponding to International Patent Application No. PCT/CN2008/000674 dated Jan. 8, 2009.
Katre, "The conjugation of proteins with polyethylene glycol and other polymers: Altering properties of proteins to enhance their therapeutic potential," Advanced Drug Delivery Reviews. vol. 10 pp. 91-114 (1993).
Katre et al., "Chemical modification of recombinant interleukin 2 by polyethylene glycol increases its potency in the murine Meth A sarcoma model," PNAS. vol. 84 p. 1487 (1987).

(Continued)

*Primary Examiner* — Jeanette Lieb
(74) *Attorney, Agent, or Firm* — Jenkins, Wilson, Taylor & Hunt, P.A.

(57) ABSTRACT

The growth hormone with high biological activity modified by the double-stranded polyethylene glycol at a single site and the preparation method thereof are provided. The PEGylated growth hormone has a higher biological activity and a longer half-life than the unmodified growth hormone. The composition comprising the PEGylated growth hormone is useful in the treatment of the growth or development disorder such as growth hormone deficiency, Turner syndrome etc.

64 Claims, 11 Drawing Sheets

(56) References Cited

OTHER PUBLICATIONS

Martial et al., "Human Growth Hormone: Complementary DNA Cloning and Expression in Bacteria," Science. vol. 205 pp. 602-607 (1979).
Neely, E.K., and Rosenfeld, R.G., "Use and Abuse of Human Growth Hormone," Annual Review of Medicine. vol. 45 pp. 407-420 (1994).
*Pharmacopoeia of the People's Republic of China*, version 2005, vol. 2, Appendix XII P.
*Pharmacopoeia of the People's Republic of China*, version 2005, vol. 3, Appendix XIV.
Roskam, W.G., and Rougeon, F., "Molecular cloning and nucleotide sequence of the human growth hormone structural gene," Nucleic Acids Research. vol. 7, No. 2 pp. 305-320 (1979).
Satake-Ishikawa et al., "Chemical Modification of Recombinant Human Granulocyte Colony-Stimulating Factor by Polyethylene Glycol Increases its Biological Activity in vivo," Cell Structure and Function. vol. 17 pp. 157-160 (1992).
Tsutsumi et al., "Chemical Modification of Natural Human Tumor Necrosis Factor-α with Polyethylene Glycol Increases Its Antitumor Potency," Japanese Journal of Cancer Research. vol. 85 pp. 9-12 (1994).
Wang et al., "Identification of the Major Positional Isomer of Pegylated In terferon Alpha-2b," Biochemistry. vol. 39, No. 35 pp. 10634-10640 (2000).
Wang et al., "Structural and biological characterization of pegylated recombinant interferon alpha-2b and its therapeutic implications," Advanced Drug Delivery Reviews. vol. 54 pp. 547-570 (2002).

* cited by examiner

Plate1

Plate2

Plate1

Plate2

DOUBLE-STRANDED POLYETHYLENE GLYCOL MODIFIED GROWTH HORMONE, PREPARATION METHOD AND APPLICATION THEREOF

TECHNICAL FIELD

The invention belongs to the field of biological preparation technology, in particular to a double-stranded polyethylene glycol (PEG) modified growth hormone (GH) with high biological activity, and the preparation method thereof, as well as the use of the obtained PEGylated growth hormone in the pharmaceutical field.

BACKGROUND ART

Human growth hormone (HuGH) is a protein hormone secreted by human anterior pituitary gland, the precursor of which consists of 217 amino acid residues, wherein the first 26 amino acid residues compose a signal peptide, and the remaining 191 amino acid residues compose the mature molecule. There are two intra-molecular disulfide bonds (Cys79 and Cys191, Cys208 and Cys215), and the molecule is not glycosylated with a molecular weight of 22 kiloDaltons (kDa). The sequence of the HuGH is set forth in SEQ ID NO: 1 (NCBI: P01241, AAA72260; Denoto F M, et al. Human growth hormone DNA sequence and mRNA structure: possible alternative splicing. *Nucleic Acids Res.*, 9: 3719-3730, 1981; Roskam W, et al. Molecular cloning and nucleotide sequence of the human growth hormone structural gene. *Nucleic Acids Res.*, 7: 305-320, 1979; Martial J A, et al. Human growth hormone: Complementary DNA cloning and expression in bacteria. *Science*, 205: 602-607, 1979; Chen E Y, et al. The human growth hormone locus: nucleotide sequence, biology and evolution. *Genomics*, 4: 479-497, 1989). The primary functions of the HuGH include promoting the growth of a cell, organ or bone, and it is closely related to the anabolism of the body (Iglesias P, et al. Recombinant human growth hormone therapy in malnourished dialysis patients: a randomized controlled study. *Am. J. Kidney Dis.*, 32(3): 454-463, 1998; Neely E K, Use and abuse of human growth hormone. *Annu. Rev. Med.*, 45:407-410, 1994). After more than 20 years' clinical application of the recombinant human growth hormone (rHuGH) produced by recombinant DNA technology, the clinical efficacy and safety of the rHuGH have been demonstrated.

The results from many researches have indicated that, rHuGH shows significant therapeutic effects in treating dwarfism, burn, wound, bone fracture, bleeding ulcer, renal failure, AIDS, anabolic disorders, endogenous growth hormone deficiency dwarfism, Turner syndrome and adult growth hormone deficiency, and it also shows significant effect in anti-aging therapy. Currently rHuGH is the only effective drug for the treatment of dwarfism. By March 2001, the indications that have been approved by FDA to enter clinical research of rHuGH include: nitrogen retention intensive treatment of severe burn, short bowel syndrome (administered alone or in combination with glutamine), AIDS related growth arrest etc. Currently, the indications of rHuGH that have been approved for marketing include: adolescent endogenous growth hormone deficiency dwarfism, Turner syndrome related dwarfism, adolescent spontaneous or organ growth hormone deficiency dwarfism, Prader-Willi syndrome, premature growth disorder, AIDS related catabolic disorder, chronic renal failure related growth retardation and adult growth hormone deficiency etc.

Polyethylene glycol is an inert, nontoxic and biodegradable organic polymer, and is important in the fields of both biotechnology and pharmaceutics. PEG modification technique is to link PEG to an active protein via covalent bond. After polyethylene-glycolation (PEGylation), the properties of the protein can be significantly improved, e.g. the prolongation of drug metabolic half-life, the reduction of immunogenicity, the increase of safety, the improvement of therapeutic efficacy, the decrease of dosing frequency, the increase of drug solubility/water solubility, the increase of resistance against proteolysis, the facilitation of drug controlled release and so on (Inada et al. *J. Bioact. and Compatible Polymers*, 5, 343, 1990; Delgado, et al. Critical Reviews in Therapeutic Drug Carrier Systems, 9, 249, 1992; Katre, Advanced Drug Delivery Systems, 10, 91, 1993 and Davis et al. U.S. Pat. No. 4,179,337). It is disclosed in U.S. Pat. No. 4,179,337 that after linking PEG to a protein such as an enzyme or insulin, the immunogenicity of the protein was reduced, while simultaneously the activities of the protein were reduced as well, but at the same time the modified protein retained a certain proportion of the activities of the original unmodified protein. Such effect was also found in G-CSF (Satake-Ishikawa et al. *Cell Structure and Function*, 17, 157-160, 1992), IL-2 (Katre et al. *Proc. Natl. Acad. Sci. USA*, 84, 1487, 1987), TNF-α (Tsutsumi et al. *Jpn. J Cancer Res.*, 85, 9, 1994), IL-6 (Inoue et al. *J. Lab. Clin. Med.*, 124, 529, 1994) and CD4-IgG (Chamow et al. *Bioconj. Chem.*, 5, 133, 1994).

It is disclosed in U.S. Pat. No. 5,824,784 that a PEG modifier with an aldehyde group at the end was used to obtain a PEG-G-CSF which was modified by a single PEG at a fixed site (N-terminal amino acid of the protein). PEG-NHS modifier synthesized by N-hydroxysuccinimide (NHS) activation can form an amido bond with ε-amino group of lysine in G-CSF. PEG-NHS has a high chemical activity but poor selectivity, and thus it is difficult to obtain a product modified by a single PEG at a fixed site. Comparing to a multi-PEGs modified product, mono-PEG modified product is more homogeneous and thus is beneficial for separation and purification, which therefore facilitates the quality control and ensures stability among batches in large-scale production.

Currently some kinds of PEGylated therapeutic protein drugs, such as PEGylated-adenosine deaminase (ADA-GEN®, Enzon Pharmaceuticals), PEGylated L-asparaginase (ONCAPSPAR®, Enzon Pharmaceuticals), PEGylated interferon-α2b (PEGINTRON™, Schering-Plough) and PEGylated interferon-α2a (Pegasys, Roche), PEGylated granulocyte colony-stimulating factor (NEULASTA®, Amgen), have been applied clinically. The in vivo metabolism of the PEG moiety in a drug (or PEG itself) has already been clearly understood, and PEG has been proven to be a good and safe drug modifier without any adverse effect.

The PEG that can be linked to a protein drug normally need to be derivatized, so that one or two terminal groups at the ends of PEG can be chemically activated to possess a proper functional group which displays activity to, and thus can form a stable covalent bond with, at least one functional group of the drug to be linked. For example, PEG can be linked to ε-$NH_2$ of a Lys residue within the protein peptide chain, or to α-$NH_2$ of the N-terminal amino acid residue of the protein peptide chain. There are normally three forms of polyethylene glycols that have been used to modify a protein: a linear chain molecule (EP 0593868; Yu-Sen Wang et al. *Advanced Drug Delivery Reviews*, 54: 547-570, 2002; Yu-Sen Wang et al. *Biochemistry*, 39, 10634-10640, 2000), U-shaped branched molecule (EP 0809996) and Y-shaped branched molecule (CN1243779C, EP1496076). The Europe Patent no. EP0809996 describes the PEGylation of IFN-α.

It is generally believed in the art that, after PEG modification, the properties of most proteins will undergo the following changes: 1. the immunogenicity and antigenicity decrease; 2. the cyclic half-life is prolonged; 3. the solubility is increased; 4. the protein is tolerant to proteolysis; 5. the biological availability is increased; 6. the toxicity is decreased; 7. the thermostability and mechanical stability are increased; 8. The isoelectric point, electrophoretic behavior, and dynamic properties are changed, etc. Furthermore, one of the most important points is that PEG modification will result in the decrease of cellular activities of a protein, which is mainly due to the groups that have been introduced into the final product, including PEG and the linkages between PEG and the protein to be modified, and also related to the conditions of coupling as well as the generated side-product. Doris Brugger et al. (US Patent, Pub. No.: US 2004/0223950 A1) discloses that the modification products of interferon-α2a mono-modified by a single double stranded UPEG at one of different sites show significantly different in vitro anti-viral activities, wherein the modification product mono-modified by UPEG at site Lys31 has the highest specific activity, while the product mono-modified by UPEG at site Lys121 has the lowest specific activity, wherein the difference between both can be up to 5 times.

Li, Weihua et al. (China Patent Pub. No.: CN 1477126A) discloses a method of preparing a PEG modified growth hormone. It is preferred to perform the modification reaction of growth hormone by branched PEG (mPEGn-NHS) at pH 6.5-7.0, and the biological activity of the purified growth hormone mono-modified by branched PEG at a single site was measured using rats with the pituitary glands removed. The results demonstrate that, PEG coupled growth hormone (wherein PEG is double stranded PEG-NHS with a molecular weight of 40 kDa) has comparable weight increasing effect to the equal amount of growth hormone injected daily.

SUMMARY OF THE INVENTION

The invention provides a method of preparing a double-stranded PEGylated growth hormone, comprising:

a) in a solution with a pH not lower than 6.0, preferably not lower than 7.0, preferably not lower than 8.0, preferably not lower than 9.0, preferably not lower than 9.5, preferably not lower than 10.0, most preferably pH 10.5, bringing U-shaped or Y-shaped branched double-stranded PEG into contact with growth hormone, preferably human growth hormone, preferably the molar ratio of the growth hormone to the double-stranded PEG being about 1:2;

b) assaying the product modified by PEG at a single site obtained in step a) in SDS-PAGE of appropriate concentration, preferably 12% SDS-PAGE, wherein the product shows two bands or is mainly one band of lower apparent molecular weight;

c) separating and recovering the product of lower apparent molecular weight in said two bands which is modified by the PEG at a single site;

optionally comprising a purification step, preferably using gel chromatography such as Q Sepharose FF chromatography, DEAE Sepharose FF chromatography or MacroCap SP chromatography.

In a preferred embodiment, the invention provides a method of preparing a double-stranded PEGylated growth hormone, wherein said double-stranded PEG is Y-shaped branched PEG of the following structural formula (I),

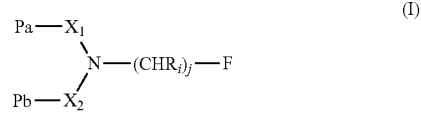

wherein, $P_a$ and $P_b$ are same or different PEG; j is an integer from 1 to 12; $R_i$ is H, substituted or unsubstituted $C_{1-12}$ alkyl, substituted aryl, aralkyl, or heteroalkyl; $X_1$ and $X_2$ are independently linking group, wherein $X_1$ is $(CH_2)_n$, $X_2$ is selected from the group consisting of: $(CH_2)n$, $(CH_2)_nOCO$, $(CH_2)_nNHCO$, $(CH_2)_nCO$, wherein n is an integer from 1 to 10; F is a terminal group selected from the group consisting of: hydroxyl, carboxyl, ester group, acyl chloride, hydrazide, maleimide, pyridine disulfide, capable of reacting with an amino, hydroxyl or hydrosulfide group of a therapeutic agent or substrate to form a covalent bond.

In a preferred embodiment, the invention provides a method of preparing a double-stranded PEGylated growth hormone, wherein the Y-shaped PEG is of the following structural formula (II):

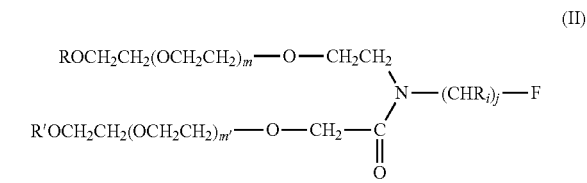

wherein, R and R' are independently low molecular weight alkyl, preferably $C_1$-$C_4$ alkyl, most preferably methyl; m and m' denote the degree of polymerization and can be any integer; m+m' is preferably from 600 to 1500; j is an integer from 1 to 12; $R_i$ is H, substituted or unsubstituted $C_{1-12}$ alkyl, substituted aryl, aralkyl or heteroalkyl; F is a terminal group selected from the group consisting of: hydroxyl, carboxyl, ester group, acyl chloride, hydrazide, maleimide, pyridine disulfide, capable of reacting with an amino, hydroxyl or hydrosulfide group of a therapeutic agent or substrate to form a covalent bond.

In a preferred embodiment, the invention provides a method of preparing a double-stranded PEGylated growth hormone, wherein the Y-shaped PEG is of the following structural formula (III):

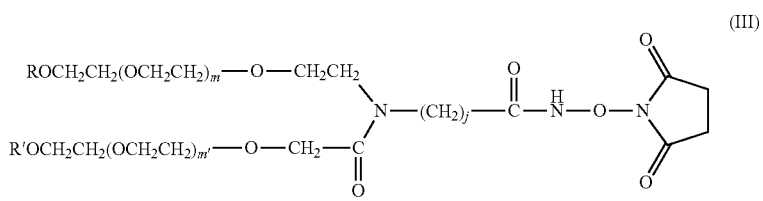

wherein, R and R' are independently low molecular weight alkyl, preferably $C_1$-$C_4$ alkyl, most preferably methyl; m and m' denote the degree of polymerization and can be any integer; m+m' is preferably from 600 to 1500, most preferably 910; the average total molecular weight of the Y-shaped PEG is from about 26 kDa to 60 kDa, preferred 40 kDa; j is an integer from 1 to 12.

In a preferred embodiment, the invention provides a method of preparing a double-stranded PEGylated growth hormone, wherein the double-stranded PEG is U-shaped PEG of the following structural formula (IV),

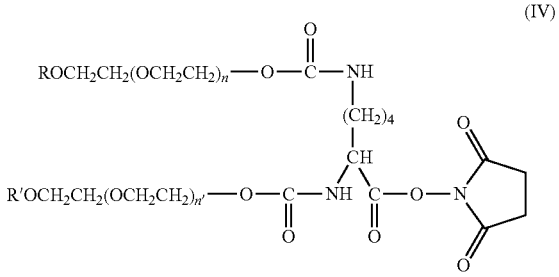

(IV)

wherein, R and R' are independently low molecular weight alkyl, preferably $C_1$-$C_4$ alkyl; n and n' denote the degree of polymerization and can be any integer; n+n' is preferably from 600 to 1500, most preferably 910; the average molecular weight of the U-shaped PEG is from about 26 kDa to 66 kDa, most preferably about 40 kDa.

In a preferred embodiment, the invention provides a method of preparing a double-stranded PEGylated growth hormone, comprising:

a) in a solution with pH 9.0 or 10.5, bringing the PEG of the following formula (III) into contact with human growth hormone, wherein the molar ratio of the growth hormone to the double-stranded PEG is about 1:2;

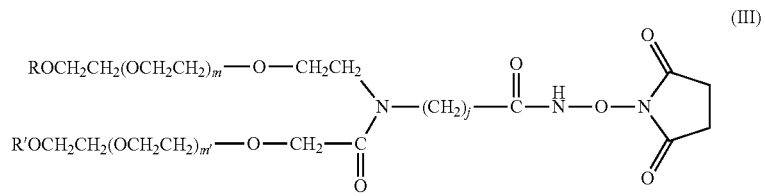

(III)

wherein, R and R' are independently low molecular weight alkyl, preferably $C_1$-$C_4$ alkyl, most preferably methyl; m+m' is 910; j is an integer from 1 to 12; the average total molecular weight of the PEG is about 40 kDa;

b) assaying the product modified by the PEG at a single site obtained in step a) in 12% SDS-PAGE, wherein the product shows two bands;

c) purifying, separating and recovering the product of lower apparent molecular weight which is modified at a single site, by using gel chromatography selected from Q Sepharose FF chromatography, DEAE Sepharose FF chromatography or MacroCap SP chromatography.

The invention also provides a PEGylated growth hormone prepared according to the above described method, wherein the growth hormone is extracted from a natural source or is a recombinant growth hormone obtained by the recombinant biotechnology, preferably the growth hormone has the sequence of SEQ ID NO:1.

In a preferred embodiment, the invention provides a PEGylated growth hormone of the following formula (VII), which is prepared according to the above described method and has the molecular weight of 62 kDa:

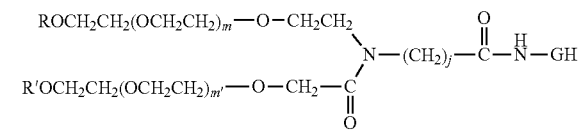

(VII)

wherein, R and R' are independently low molecular weight alkyl, preferably $C_1$-$C_4$ alkyl, most preferably methyl; M+m' is 910; and j is an integer from 1 to 12.

The invention also provides a method of preparing a PEGylated growth hormone preparation, comprising:

a) in a solution with a pH not lower than 8.0, preferably not lower than 9.0, preferably not lower than 9.5, preferably not lower than 10.0, most preferably pH 10.5, bringing U-shaped or Y-shaped branched double-stranded PEG into contact with growth hormone, preferably human growth hormone, preferably the molar ratio between the growth hormone and the double-stranded PEG being about 1:2;

b) assaying the product modified by the PEG at a single site obtained in step a) in SDS-PAGE of appropriate concentration, preferably 12% SDS-PAGE, wherein the product shows two bands;

c) separating and recovering the product modified by the PEG at a single site;

said recovered product is a mixture that predominantly comprises the product of lower apparent molecular weight which is modified by the PEG at a single site, wherein the content of the product of lower apparent molecular weight which is modified by the PEG at a single site, detected by SDS-PAGE, is not lower than 70%, preferably not lower than 80%, most preferably not lower than 90%, optionally comprising a purification step, preferably using gel chromatography such as Q Sepharose FF chromatography, DEAE Sepharose FF chromatography or MacroCap SP chromatography.

In a preferred embodiment, the invention provides a method of preparing a double-stranded PEGylated growth hormone preparation, wherein the double-stranded PEG is Y-shaped PEG of the following structural formula (I),

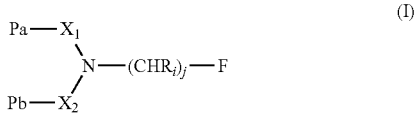
(I)

wherein, $P_a$ and $P_b$ are same or different PEG; j is an integer from 1 to 12; $R_i$ is H, substituted or unsubstituted $C_{1-12}$ alkyl, substituted aryl, aralkyl, or heteroalkyl; $X_1$ and $X_2$ are independently linking group, wherein $X_1$ is $(CH_2)_n$, $X_2$ is selected from the group consisting of: $(CH_2)n$, $(CH_2)_nOCO$, $(CH_2)_nNHCO$, $(CH_2)_nCO$, wherein n is an integer from 1 to 10; F is a terminal group selected from the group consisting of: hydroxyl, carboxyl, ester group, acyl chloride, hydrazide, maleimide, pyridine disulfide, capable of reacting with an amino, hydroxyl or hydrosulfide group of a therapeutic agent or substrate to form a covalent bond.

In a preferred embodiment, the invention provides a method of preparing a double-stranded PEGylated growth hormone preparation, wherein the Y-shaped PEG is of the following structural formula (II):

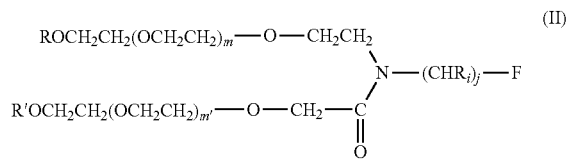
(II)

wherein, R and R' are independently low molecular weight alkyl, preferably $C_1$-$C_4$ alkyl, most preferably methyl; m and m' denote the degree of polymerization and can be any integer; M+m' is preferably from 600 to 1500, most preferably 910; j is an integer from 1 to 12; $R_i$ is H, substituted or unsubstituted $C_{1-12}$ alkyl, substituted aryl, aralkyl, or heteroalkyl; F is a terminal group selected from the group consisting of: hydroxyl, carboxyl, ester group, acyl chloride, hydrazide, maleimide, pyridine disulfide, capable of reacting with an amino, hydroxyl or hydrosulfide group of a therapeutic agent or substrate to form a covalent bond.

In a preferred embodiment, the invention provides a method of preparing a double-stranded PEGylated growth hormone preparation, wherein the Y-shaped PEG is of the following structural formula (III):

wherein, R and R' are independently low molecular weight alkyl, preferably $C_1$-$C_4$ alkyl, most preferably methyl; m and m' denote the degree of polymerization and can be any integer; m+m' is preferably from 600 to 1500, most preferably 910; j is an integer from 1 to 12; preferably the average total molecular weight of the PEG is from about 26 kDa to 60 kDa, preferably 40 kDa.

In a preferred embodiment, the invention provides a method of preparing a double-stranded PEGylated growth hormone preparation, wherein the double-stranded PEG is U-shaped PEG of the following structural formula (IV),

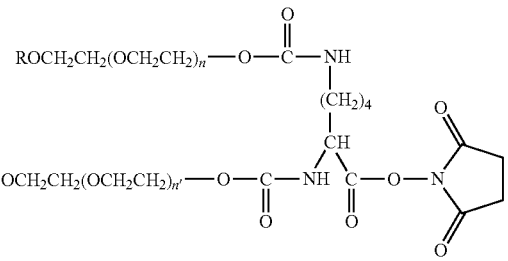

wherein, R and R' are independently low molecular weight alkyl, preferably $C_1$-$C_4$ alkyl; n and n' denote the degree of polymerization and can be any integer; n+n' is preferably from 600 to 1500, most preferably 910; the average molecular weight of the U-shaped PEG is from about 26 kDa to 66 kDa, most preferably about 40 kDa.

In a preferred embodiment, the invention also provides a method of preparing a double-stranded PEGylated growth hormone preparation, comprising:

a) in a solution with pH 9.0 or 10.5, bringing the PEG of the following formula (III) into contact with human growth hormone, wherein the molar ratio of the growth hormone to the double-stranded PEG is about 1:2;

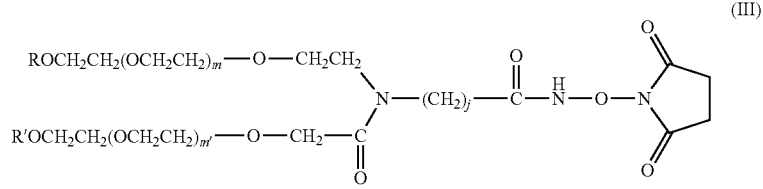
(III)

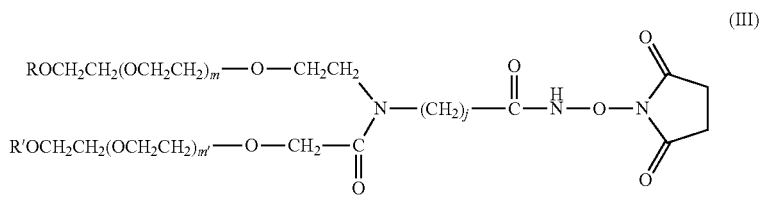

(III)

wherein, R and R' are independently low molecular weight alkyl, preferably $C_1$-$C_4$ alkyl; m+m' is 910, j is an integer from 1 to 12; the average total molecular weight of the PEG is about 40 kDa;

b) assaying the product modified by the PEG at a single site obtained in step a) in 12% SDS-PAGE;

c) seperating and recovering the product modified by the PEG at a single site by using gel chromatography selected from Q Sepharose FF chromatography, DEAE Sepharose FF chromatography or MacroCap SP chromatography, and the SDS-PAGE content of the product of lower apparent molecular weight, which is modified by the PEG at a single site, in the recovered product is not lower than 70%, preferably not lower than 80%, most preferably not lower than 90%.

The invention also provides a PEGylated growth hormone perparation prepared according to the above described method, wherein the growth hormone is extracted from a natural source or is a recombinant growth hormone obtained by the recombinant biotechnology, preferably the growth hormone has the sequence of SEQ ID NO:1. Preferably, the product modified by the PEG at a single site in the PEGylated growth hormone preparation is of the following formula (VII):

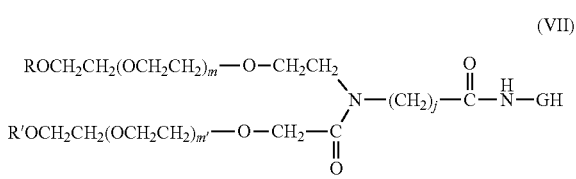

(VII)

wherein, R and R' are independently low molecular weight alkyl, preferably $C_1$-$C_4$ alkyl, most preferably methyl; M+m' is 910, j is an integer from 1 to 12, wherein the SDS-PAGE content of the product of lower apparent molecular weight which is modified by the PEG at a single site in the PEGylated growth hormone preparation is not lower than 70%, preferably not lower than 80%, most preferably not lower than 90%.

In a preferred embodiment of the invention, the recombinant human growth hormone is artificially synthesized or expressed from an expression system selected from the group consisting of: a prokaryotic system such as *E. coli*, a eukaryotic system such as yeast *Pichia*; an insect cell system, and a mammalian cell system such as CHO cell.

The invention also provides a composition comprising a pharmaceutically effective amount of the above described PEGylated growth hormone or the PEGylated growth hormone preparation and a pharmaceutically acceptable carrier or excipient, preferably comprising mannitol, an amino acid, sodium chloride, acetic acid or sodium acetate, preferably the amino acid is selected from the group consisting of aspartate, asparagine, lysine and glycine.

The invention also provides the use of the above described PEGylated growth hormone or the PEGylated growth hormone preparation or the composition in the manufacture of a medicament for the treatment of a disease in need of the growth hormone treatment or for anti-aging treatment, preferably the disease in need of growth hormone treatment is selected from the group consisting of dwarfism, burn, wound, bone fracture, bleeding ulcer, renal failure, AIDS, endogenous growth hormone deficiency dwarfism, Turner syndrome, anabolic disorder and adult growth hormone deficiency.

The invention also provides a method of treating a patient with a disease in need of growth hormone treatment or for anti-aging treatment, the method comprising administering a therapeutically effective amount of the above described PEGylated growth hormone or the PEGylated growth hormone preparation or the composition to said patient, preferably the disease in need of growth hormone treatment is selected from the group consisting of dwarfism, burn, wound, bone fracture, bleeding ulcer, renal failure, AIDS, endogenous growth hormone deficiency dwarfism, Turner syndrome, anabolic disorder and adult growth hormone deficiency.

DETAILED DESCRIPTION OF THE INVENTION

The invention provides double-stranded polyethylene glycol (PEG) modified growth hormone with high biological activity, and the preparation method thereof. The notable feature of this invention lies in that, after optimizing the reaction condition and the separation method, the content of the low cellular activity component in the growth hormone modified by PEG at a single site is significantly decreased. In one example of the double-stranded PEG with a molecular weight of 40 kDa, the product of low cellular activity modified at a single site is characterized in that, this product and the product of high cellular activity modified at a single site are completely separated into two bands in 12% SDS-PAGE, and the apparent molecular weight of the product of low cellular activity modified at a single site is higher than that of the product of high cellular activity modified at a single site. Using rat with its pituitary glands removed as an animal model and the recombinant human growth hormone as a positive control, the in vivo biological activity of the product of high cellular activity modified at a single site is assayed according to the growth hormone bioassay as described in *Pharmacopoeia of the People's Republic of China*, version 2005, Volume 2, Appendix XII P. The product of high cellular activity modified at single site has a significantly higher biological specific activity than the normal growth hormone, exhibiting more than 1.5 times of biological activity of the normal growth hormone, and it is shown in the pharmacokinetic research in crab-eating macaque (*Macaca fascicularis*) that it has an average drug metabolic half-life in serum of more 20 times longer than that of the normal growth hormone, and thus has long-term effects.

In one embodiment of the invention, the double stranded PEG-NHS modification reaction for growth hormone is performed at pH8.0, SDS-PAGE electrophoresis is used to assay the products of the reaction, and silver staining is used for visualization. It is surprised that, the growth hormone product modified by PEG at a single site shows two major bands, which is different from previous reports (Ross Clark, Kenneth Olson, et al. Long-acting growth hormones produced by conjugation with polyethylene glycol. *J. Biol. Chem.*, 271:21969-21977, 1996. Li, Weihua, Dong Jian et al., Long-term effective growth hormone and the pharmacological composition, China Patent Pub. No.: CN1477126A). In further experiments, the modifications of the growth hormone by double stranded PEG-NHS performed in a range of pH6.0-10.5 have been studied, and it is found by SDS-PAGE that all the products modified at a single site show two major bands. As the pH increases, the content of the band of lower apparent molecular weight also increases. At pH≥10.0, the product modified at a single site shows substantially one band of lower apparent molecular weight.

In one preferred embodiment of the invention, some appropriate gel chromatography purification techniques are used to prepare the purified recombinant human growth hormone modified by PEG at a single site at pH10.5 and pH6.0 respectively. SDS-PAGE with 12% separation gel is used for detection, and silver staining is used for visualization. The purified recombinant human growth hormone modified by PEG at a single site at pH6.0 clearly shows two bands. The purified recombinant human growth hormone modified by PEG at a single site at pH10.5 shows mainly the band of lower apparent molecular weight, the SDS-PAGE content of which is not lower than 80%. Only trace amount of the substrate protein is detected in both cases (no more than 0.5%). MALDI-TOF MS confirms that the modified products at the two pH conditions are substantially the growth hormone products modified by PEG at a single site. The cellular activity assay indicates that the product modified at a single site at pH10.5 has a significantly higher cellular activity than the product modified at a single site at pH6.0, the cellular specific activity of the former is about two times of that of the latter.

In one preferred embodiment of the invention, the purified modification product of the recombinant human growth hormone, which is modified by PEG at a single site at pH6.0 and has a higher apparent molecular weight, is prepared by Q Sepharose FF chromatography purification or MacroCap SP chromatography purification etc. MALDI-TOF MS detection confirms that the PEG modified recombinant human growth hormone is a product modified by PEG at a single site, and the cellular activity assay has shown that its cellular specific activity is significantly lower than that of the purified recombinant human growth hormone modified at a single site (with a lower apparent molecular weight) at pH10.5. The cellular specific activity of the latter is up to 3 times of the former.

In a further embodiment of the invention, according to the bioassay for growth hormone as described in *Pharmacopoeia of the People's Republic of China*, version 2005, Volume 3, Appendix XII P, using recombinant human growth hormone as the positive control, the method employing a rat with pituitary gland removed is used to assay the in vivo biological activity of the modification products of the recombinant human growth hormone modified by PEG-NHS of 40 kDa at a single site at pH 10.5. The recombinant human growth hormone is administered once everyday, 6 times in total. The product of the recombinant human growth hormone modified by PEG at a single site is administered once in a dose as same as the sum of 6 times administration of the recombinant human growth hormone. The recombinant human growth hormone modified by PEG at a single site has a significantly higher biological activity than the recombinant human growth hormone, and can reach up to a biological specific activity of more than 1.5 times of the latter. Its pharmacology has a long-term effect. The pharmacokinetic research in crab-eating macaque has shown that the drug metabolic half-life of the recombinant human growth hormone modified by PEG at a single site is elongated more 20 times than that of the normal recombinant growth hormone.

The invention employs branched (U-shaped branched and Y-shaped branched) PEG derivatives to modify growth hormone. The Y-shaped branched PEG derivative employed in the invention is a novel branched PEG derivative, the structure of which is different from linear PEG or U-shaped branched PEG, and its main difference from U-shaped branched PEG lies in that the two branched PEG chains of the Y-shaped PEG derivative of the present invention are linked together through N atom, whereas the two branched PEG chains of the U-shaped PEG derivative are linked together through C atom. The modification with U-shaped or Y-shaped PEG mainly occur at the N-terminal free α-amino of a protein or peptide or at ε-amino of the side chain of a Lys residue. The Y-shaped PEG derivative is of the following molecular formula (I):

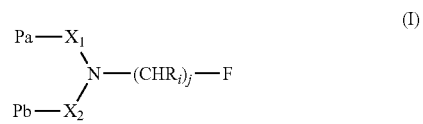

wherein, $P_a$ and $P_b$ are same or different PEG; j is an integer from 1 to 12; $R_i$ is H, substituted or unsubstituted $C_{1-12}$ alkyl, substituted aryl, aralkyl, or heteroalkyl; $X_1$ and $X_2$ are independently linking group respectively, wherein $X_1$ is $(CH_2)_n$, $X_2$ is selected from the group consisting of: $(CH_2)n$, $(CH_2)_nOCO$, $(CH_2)_nNHCO$, $(CH_2)_nCO$, wherein n is an integer from 1 to 10; F is a terminal group selected from the group consisting of: hydroxyl, carboxyl, ester group, acyl chloride, hydrazide, maleimide, pyridine disulfide, capable of reacting with an amino, hydroxyl or hydrosulfide group of a therapeutic agent or substrate to form a covalent bond.

In one preferred embodiment of the invention, the $P_a$ and $P_b$ of the Y-shaped PEG derivative can be same or different PEG, as shown in formula (II):

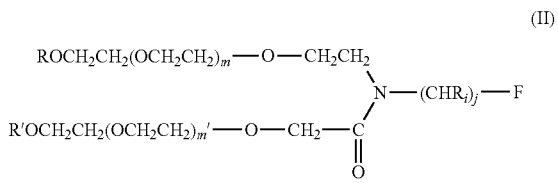

wherein, R and R' are independently low molecular weight alkyl, preferably $C_1$-$C_4$ alkyl, most preferably methyl; m and m' denote the degree of polymerization and can be any integer; m+m' is preferably from 600 to 1500, most preferably 910; $R_1$ is H, substituted or unsubstituted $C_{1-12}$ alkyl, substituted aryl, aralkyl, or heteroalkyl; j is an integer from 1 to 12. F is a terminal group selected from the group consisting of: hydroxyl, carboxyl, ester group, acyl chloride, hydrazide, maleimide, pyridine disulfide, capable of reacting with an amino, hydroxyl or hydrosulfide group of a therapeutic agent or substrate to form a covalent bond. Preferably, the average total molecular weight of the PEG is about from 26 kDa to 60 kDa, most preferably 40 kDa.

In one embodiment, the invention provides a PEGylated growth hormone of the following structure formula (VI):

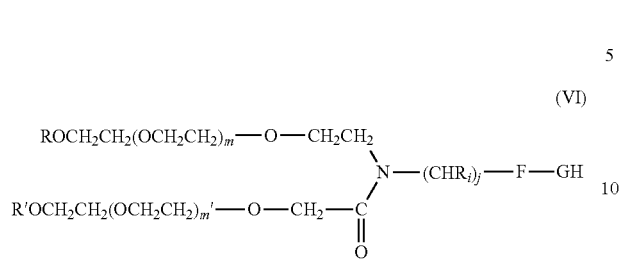

(VI)

wherein, R and R' are independently low molecular weight alkyl, preferably $C_1$-$C_4$ alkyl, most preferably methyl; j is an integer from 1 to 12; m and m' denote the degree of polymerization and can be any integer; M+m' is preferably from 600 to 1500; $R_i$ is H, substituted or unsubstituted $C_{1-12}$ alkyl, substituted aryl, aralkyl, or heteroalkyl; F is a terminal group selected from the group consisting of: hydroxyl, carboxyl, ester group, acyl chloride, hydrazide, maleimide, pyridine disulfide, capable of reacting with an amino, hydroxyl or hydrosulfide group of a therapeutic agent or substrate to form a covalent bond. In one preferred embodiment of the invention, the structure of the Y-shaped PEG derivative molecule (YPEG-NHS) is shown in the following formula (III):

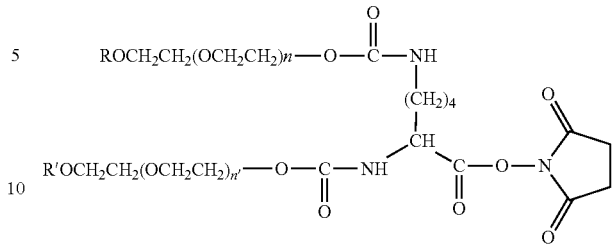

(IV)

wherein, R and R' are independently low molecular weight alkyl, preferably $C_1$-$C_4$ alkyl; n and n' denote the degree of polymerization and can be any integer; n+n' is preferably from 600 to 1500, most preferably 910; the average molecular weight of the PEG is about from 26 kDa to 66 kDa, most preferably about 40 kDa.

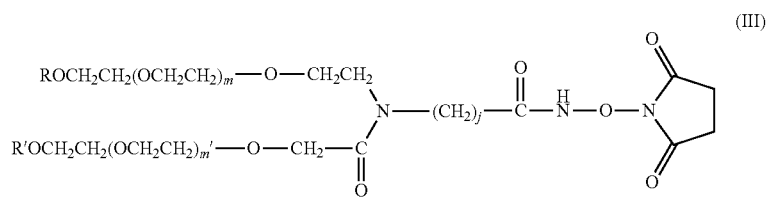

(III)

wherein, R and R' are independently low molecular weight alkyl, preferably $C_1$-$C_4$ alkyl, most preferably methyl; j is an integer from 1 to 12; m and m' denote the degree of polymerization and can be any integer; M+m' is preferably from 600 to 1500, most preferably 910.

In one preferred embodiment of the invention, the structure of the U-shaped PEG derivative molecule (UPEG-NHS) is shown in the following formula (IV):

In one embodiment of the invention, to obtain YPEG or UPEG modified GH, the PEG moiety of an activated YPEG and UPEG derivative such as PEG succinimidyl ester (YPEG-NHS) is covalently linked to an amino (—$NH_2$) of a protein through nucleophilic substitution, the —$NH_2$ includes the N-terminal α-$NH_2$ of the protein and ε-$NH_2$ of a Lys residue. The reaction equation of the production of YPEG-GH from GH and YPEG-NHS is as below:

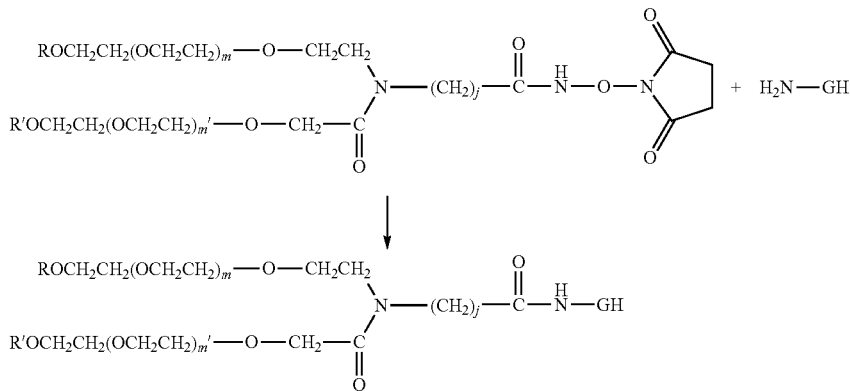

The reaction equation of the production of UPEG-GH from GH and UPEG-NHS is as below:

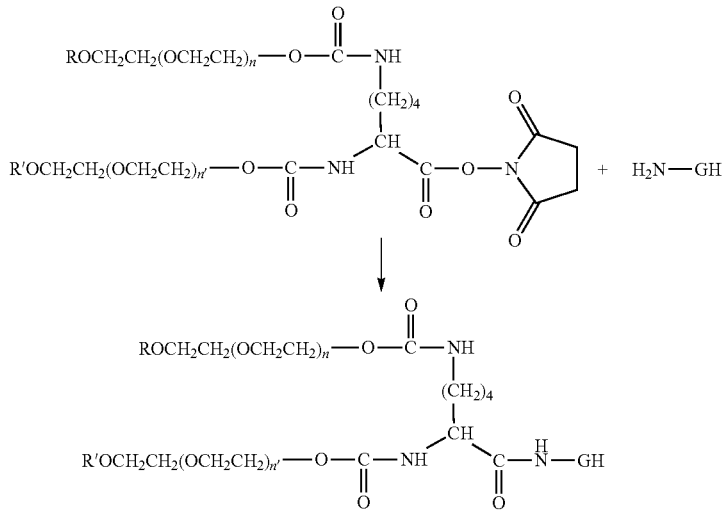

Preferably, the average total molecular weight of the PEG is about from 26 kDa to 66 kDa, most preferably about 40 kDa.

In a further preferred embodiment of the invention, the PEGylated GH of the invention is of the following structure formula (VII):

(VII)

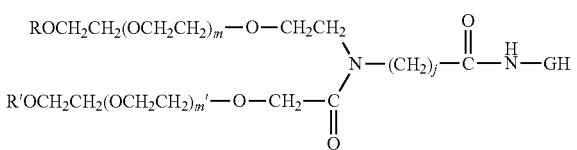

wherein, R and R' are independently low molecular weight alkyl, preferably $C_1$-$C_4$ alkyl, most preferably methyl; j is an integer from 1 to 12; m and m' denote the degree of polymerization and can be any integer; m+m' is preferably from 600 to 1500. In the structure, the Y-shaped branched PEG is linked to the GH molecule at a single site. m and m' can be same or different integer. The molecular weight of the YPEG-GH in the above formula depends on the degree of polymerization m and m'. Where m+m' is preferably from 600 to 1500, the corresponding average molecular weight of the YPEG is from about 26 kDa to about 66 kDa. Where m+m' is preferably from 795 to 1030, the corresponding average molecular weight of the YPEG is from about 35 kDa to about 45 kDa. Where m+m' is particularly preferably from 885 to 1030, the corresponding average molecular weight of the YPEG is about from 39 kDa to 45 kDa. Where m+m' is most preferably 910, the corresponding average molecular weight of the YPEG is about 40 kDa. The ratio of m to m' can be in a range from 0.5 to 1.5, preferably from 0.8 to 1.2.

Optionally, the GH of the invention can be extracted from a natural source or obtained by the recombinant biotechnology. Preferably, the GH is human GH having the sequence of SEQ ID NO:1, which is extracted from a natural source or obtained by the recombinant biotechnology. More preferably, the human GH is recombinant human GH. The GH can be artificially synthesized, or be expressed from a prokaryotic system like *E. coli*, or be expressed from a yeast system like *Pichia pastoris*, or be expressed from an insect cell system or mammalian cell system like CHO. The preparation method of the natural or recombinant GH and the activity tests of GH and PEG modified products are well known in the art.

Similar to GH, the YPEG-GH and UPEG-GH of the invention can be used clinically to treat dwarfism, burn, wound, bone fracture, bleeding ulcer, renal failure, AIDS, anabolic disorder, adult growth hormone deficiency and for anti-aging treatment. The YPEG-GH and UPEG-GH of the invention can be administered to a patient in a form of a composition comprising a pharmaceutically effective amount of the YPEG-GH or UPEG-GH, and a pharmaceutically acceptable carrier or excipient. Therefore, in another aspect, the invention provides a composition comprising a pharmaceutically effective amount of the PEGylated GH of the invention and a pharmaceutically acceptable carrier or excipient. The pharmaceutically acceptable carrier used in the invention comprises a pharmaceutically acceptable carrier, excipient or stabilizer that is non-toxic to the cell or mammalian to be contacted with it in the used dosage or concentration. Normally a physiologically acceptable carrier is an aqueous pH buffer. Examples of a physiologically acceptable carrier comprise a buffer such as phosphate, citrate, and other organic acid buffer, an antioxidant such as ascorbic acid, a polypeptide of low molecular weight (not more than 10 residues), a protein such as seralbumin, gelatin, or immunoglobulin, a hydrophilic polymer such as polyvinyl pyrrolidone, an amino acid such as glycine, aspartate, glutamine, asparagine, arginine or lysine, a monosaccharide such as glucose and mannose, other saccharides like disaccharide and dextrin etc., a chelator such as EDTA, a sugar alcohol such as mannitol and sorbitol, a salt forming counter-ion such as sodium, and/or a non-ionic surfactant such as TWEEN, PEG and PLURONICS. Excipient is preferably sterile and normally is free of a harmful substance. The composition can be sterilized using routine sterilization techniques. In one embodiment of the invention, the composition further comprises mannitol, an amino acid, sodium chloride, acetic acid and sodium acetate, wherein the amino acid is preferably selected from the group consisting of lysine, aspartate, asparagine and glycine.

In another aspect, the invention also provides the use of the PEGylated GH of the invention or the composition comprising the PEGylated GH of the invention in the preparation of a medicament for the treatment of a disease in need of GH treatment and for anti-aging treatment. Preferably, the disease in need of GH treatment is selected from the group consisting of dwarfism, burn, wound, bone fracture, bleeding ulcer, renal failure, AIDS, endogenous growth hormone deficiency dwarfism, Turner syndrome, anabolic disorder and adult growth hormone deficiency.

CONCRETE EMBODIMENTS TO CARRY OUT THE INVENTION

The present invention will be further described through the following examples, but any examples or combinations thereof should not be considered as limiting the scope and embodiments of this invention. The scope of this invention is only limited by the appended claims. Combining this description and prior art in the art, a person skilled in the art can clearly understand the scope limited by the claims.

Example 1

Figure 1:
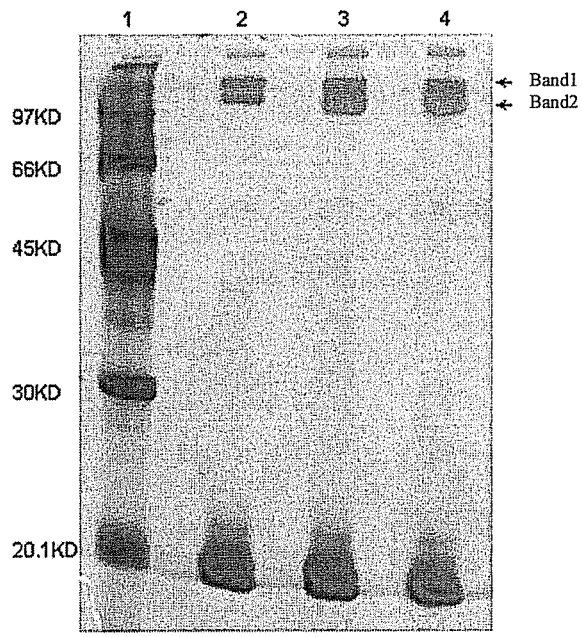
FIG. 1: The results of non-reductive SDS-PAGE of the rHuGH samples modified by YPEG-NHS 40 kDa or UPEG-NHS 40 kDa at pH 8.0. The concentration of the separation gel is 12%, and silver staining is used for visualization. Lane 1: marker, LMW, GE Healthcare; Lane 2: rHuGH sample modified by YPEG-NHS at pH 8.0, loading amount 2 μg; Lane 3: rHuGH sample modified by YPEG-NHS at pH 8.0, loading amount 5 μg; Lane 4: rHuGH sample modified by UPEG-NHS at pH 8.0, loading amount 5 μg.

The Modification of the Recombinant Human GH by U-Shaped or Y-Shaped Branched PEG 200 mg of each of UPEG-NHS and YPEG-NHS (average M.W. 40 kDa, equal-arm; lot. Nos. ZZ004P182 and ZZ004P167, respectively) (Beijing JenKem Technology Co., Ltd.) were weighted and dissolved in 2 ml of 2 mM HCl (Guangdong Guanghua Chemical Factory Co., Ltd.) respectively. 50 mg rHuGH (Xiamen Amoytop Biotech Co., Ltd.) and 50 mM boric acid-borax buffer, pH 8.0 (Sinopharm Shanghai Chemical Reagent Co., Ltd.) were added respectively to a final total reaction volume of 10 ml. In the reaction system, the final reaction concentration of rHuGH was 5 mg/ml, and the reaction molar ratio of rHuGH to PEG-NHS was about 1:2. The incubation was done at <10° C. for 2h with shaking, and glacial acetic acid (Shantou Xilong Chemical Co., Ltd.) was added to make pH <4.0 to stop the reaction. A sample was taken for SDS-PAGE, and silver staining was used for visualization. The SDS-PAGE results are shown in FIG. 1. From the SDS-PAGE results in FIG. 1, the modification products at pH 8.0 show two main bands, and the samples modified by UPEG-NHS and YPEG-NHS show the same SDS-PAGE electrophoresis characteristics.

Example 2

Figure 2:
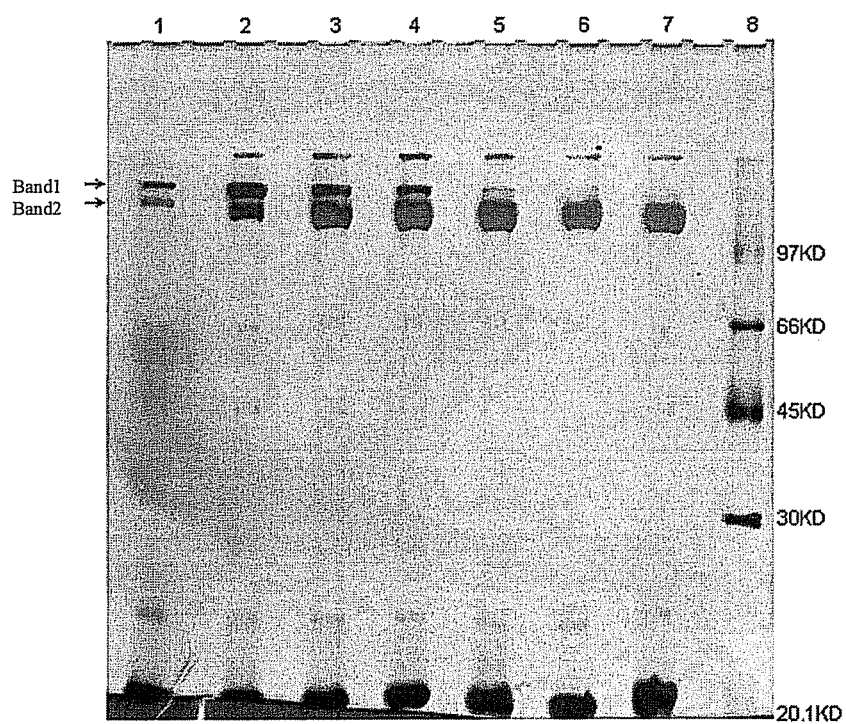
FIG. 2: The results of non-reductive SDS-PAGE of the rHuGH samples modified by YPEG-NHS 40 kDa at different pHs. The concentration of the separation gel is 12%, and silver staining is used for visualization. Lane 1: rHuGH sample modified by YPEG-NHS at pH 6.0; Lane 2: rHuGH sample modified by YPEG-NHS at pH 7.0; Lane 3: rHuGH sample modified by YPEG-NHS at pH 8.0; Lane 4: rHuGH sample modified by YPEG-NHS at pH 9.0; Lane 5: rHuGH sample modified by YPEG-NHS at pH 9.5; Lane 6: rHuGH sample modified by YPEG-NHS at pH 10.0; Lane 7: rHuGH sample modified by YPEG-NHS at pH 10.5; Lane 8: marker, LMW, GE Healthcare. The loading amount of all samples is 5 μg.
Figure 3:
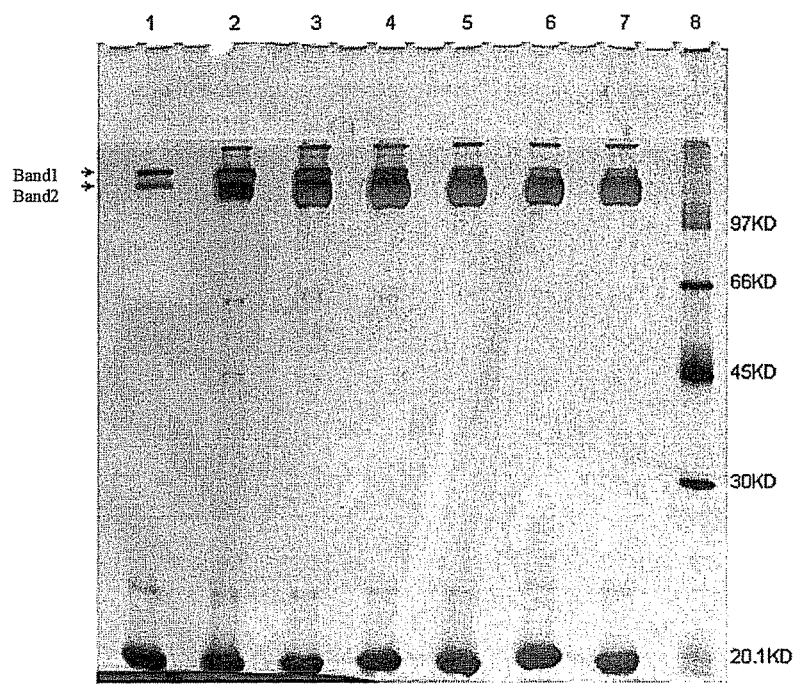
FIG. 3: The results of non-reductive SDS-PAGE of the rHuGH samples modified by UPEG-NHS at different pHs. The concentration of the separation gel is 12%, and silver staining is used for visualization. Lane 1: rHuGH sample modified by UPEG-NHS at pH 6.0; Lane 2: rHuGH sample modified by UPEG-NHS at pH 7.0; Lane 3: rHuGH sample modified by UPEG-NHS at pH 8.0; Lane 4: rHuGH sample modified by UPEG-NHS at pH 9.0; Lane 5: rHuGH sample modified by UPEG-NHS at pH 9.5; Lane 6: rHuGH sample modified by UPEG-NHS at pH 10.0; Lane 7: rHuGH sample modified by UPEG-NHS at pH 10.5; Lane 8: marker, LMW, GE Healthcare. The loading amount of all samples is 5 μg.

The Modifications of the Recombinant Human GH by U-Shaped and Y-Shaped Branched PEG at Different pHs 200 mg of each of UPEG-NHS and YPEG-NHS (average M.W. 40 kDa, equal-arm; lot. Nos. ZZ004P182 and ZZ004P167 respectively) (Beijing JenKem Technology Co., Ltd.) were weighted and dissolved in 2 ml of 2 mM HCl (Guangdong Guanghua Chemical Factory Co., Ltd.) respectively. 50 mg rHuGH (Xiamen Amoytop Biotech Co., Ltd.) and the corresponding buffer were added respectively to a final total reaction volume of 10 ml. 10 mM PBNa buffer (Sinopharm Shanghai Chemical Reagent Co., Ltd.) of the corresponding pH for the reaction at pH 6.0, 7.0 or 8.0 was used, and 50 mM borax buffer (Sinopharm Shanghai Chemical Reagent Co., Ltd.) of the corresponding pH for the reaction at pH 9.0, 9.5, 10.0 or 10.5 was used. In the reaction system, the final reaction concentration of rHuGH was 5 mg/ml, and the reaction molar ratio of rHuGH to PEG-NHS was about 1:2. Incubation was done at <10° C. for 2h with shaking, and glacial acetic acid (Shantou Xilong Chemical Co., Ltd.) was added to make pH<4.0 to stop the reaction. A sample was taken for SDS-PAGE, and silver staining was used for visualization. The gel visualization system (Model No.: FR-200, Shanghai FURI Science & Technology Co., Ltd.) was used to analyze the electrophoresis results. SDS-PAGE electrophoresis results are shown in FIG. 2 and FIG. 3, and the analysis results by the gel visualization system are shown in table 1. From the electrophoresis results, the modified products at pH 6.0-9.5 show clearly two main bands, and as the reaction pH increases, the content of the band of lower apparent molecular weight also increases correspondingly. The modified products at pH 10.0 and 10.5 are substantially the band of lower apparent molecular weight. The samples modified UPEG-NHS and YPEG-NHS show the same SDS-PAGE electrophoresis characteristics.

TABLE 1

The analysis of the gel visualization system on SDS-PAGE results of the recombinant human GHs modified by U-shaped and Y-shaped branched PEG at different pHs

| | Modification reaction pH | 6.0 | 7.0 | 8.0 | 9.0 | 9.5 | 10.0 | 10.5 |
|---|---|---|---|---|---|---|---|---|
| YPEG | Band 1 content (%) | 53.9 | 48.6 | 27.7 | 25.7 | 6.9 | 5.6 | 7.9 |
| | Band 2 content (%) | 46.1 | 51.4 | 72.3 | 74.3 | 93.1 | 94.4 | 92.1 |
| UPEG | Band 1 content (%) | 47.5 | 41.8 | 30.1 | 27.4 | 24.4 | 18.9 | 7.5 |
| | Band 2 content (%) | 52.5 | 58.2 | 69.9 | 72.6 | 75.6 | 81.1 | 92.5 |

Note:
"content" refers to the relative percentage content of band 1 (higher apparent M.W.) to band 2 (lower apparent M.W.) of the rHuGH products modified by PEG at a single site.

Example 3

The Preparation, Cellular Activity and M.W. of the Recombinant Human GH Modified by U-Shaped or Y-Shaped Branched PEG at a Single Site at pH6.0, pH9.0 or 10.5

1 Modification

Three samples of 1200 mg of each of UPEG-NHS and YPEG-NHS (average M.W. 40 kDa, equal-arm; lot. Nos. ZZ004P182 and ZZ004P167 respectively) (Beijing JenKem Technology Co., Ltd.) were weighted and dissolved in 12 ml of 2 mM HCl (Guangdong Guanghua Chemical Factory Co., Ltd.) respectively. 300 mg of rHuGH (Xiamen Amoytop Biotech Co., Ltd.) and 50 mM borax buffer (pH10.5) or 50 mM boric acid/borax buffer (pH9.0) or 10 mM PBNa (pH6.0) (Sinopharm Shanghai Chemical Reagent Co., Ltd.) were added respectively to a final total reaction volume of 60 ml. In the reaction system, the final reaction concentration of rHuGH was 5 mg/ml, the reaction molar ratio between the rHuGH and the PEG-NHS was about 1:2, and the reaction pHs were 10.5, 9.0 and 6.0 respectively. Incubation was done at <10° C. for 2h with shaking, and glacial acetic acid (Shantou Xilong Chemical Co., Ltd.) was added to make pH<4.0 to stop the reaction. A sample was taken for SDS-PAGE, and silver staining was used for visualization.

2 Purification 2.1 Q Sepharose FF Chromatography Purification

The PEG modification sample of rHuGH was diluted 3 times using ultrapure water, and the pH of the diluted sample was adjusted to 9.0 with NaOH or HCl.

2.1.1 The Q Sepharose FF Chromatography Purification of the PEG Modification Samples (pH6.0) of rHuGH The chromatography column (Shanhai Jinhua Chromatography Equipment Factory) was Φ18 mm×400 mm, the packing specification of the Q Sepharose FF packing material (GE Healthcare) was Φ18 mm×240 mm, and the volume of the column bed (CV) was 61 ml. The Q Sepharose FF chromatography column was cleaned-in-place using 0.5M NaOH at 5 ml/min for 30 min, eluted with 3 CV of $ddH_2O$ at 5 ml/min, regenerated with 3 CV of 1M NaCl at 5 ml/min, and eluted with κCV of 20 mM boric acid/borax-17 mM NaCl (pH 9.0, solution A) at 5 ml/min. The ultrapure water diluted samples of the PEG modified rHuGH was loaded at a flow rate of 3 ml/min, and the eluent was detected at 280 nm (AKTA Basic100, GE Healthcare). Elution was done using solution A at 5 ml/min until the first peak was completely detected; and 20 mM boric acid/borax-100 mM NaCl (pH 9.0, solution B) was then used to elute at 5 ml/min until the second peak was completely detected. 20 mM boric acid/borax-200 mM NaCl (pH 9.0, solution C) was then used to elute at 5 ml/min until the third peak was completely detected. The sample from the second peak was collected as the target sample. The buffer system of the target sample was changed to 20 mM boric acid/borax (pH9.0) through ultrafiltration with 5K ultrafilter (Millipore, polyethersulfone material).

2.1.2 The Q Sepharose FF Chromatography Purification of PEG Modification Samples (pH9.0 or 10.5) of rHuGH The chromatography column (Shanhai Jinhua Chromatography Equipment Factory) was Φ18 mm×400 mm, the packing specification of the Q Sepharose FF packing material (GE Healthcare) was φ18 mm×240 mm, and the volume of the column bed (CV) was 61 ml. The Q Sepharose FF chromatography column was cleaned-in-place using 0.5M NaOH at 5 ml/min for 30 min, eluted with 3 CV of $ddH_2O$ at 5 ml/min, regenerated with 3 CV of 1M NaCl at 5 ml/min, and eluted with 5 CV of 20 mM boric acid/borax-17 mM NaCl (pH 9.0, solution A) at 5 ml/min. The ultrapure water diluted sample of PEG modified rHuGH was loaded at a flow rate of 3 ml/min, and the eluent was detected at 280 nm (AKTA Basic100, GE Healthcare). Elution was done using solution A at 5 ml/min until the first peak was completely detected, and 20 mM boric acid/borax-40 mM NaCl (pH 9.0, solution B) was used to elute at 5 ml/min until the second peak was completely detected. 20 mM boric acid/borax-100 mM NaCl (pH 9.0, solution C) was then used to elute at 5 ml/min until the third peak was completely detected, and 20 mM boric acid/borax-200 mM NaCl (pH 9.0, solution D) was used to elute at 5 ml/min until the fourth peak was completely detected. The sample from the third peak was collected as the target sample. The buffer system of the target sample was changed to 20 mM boric acid/borax (pH9.0) through ultrafiltration with 5K ultrafilter (Millipore, polyethersulfone material).

2.2 DEAE Sepharose FF Chromatography Purification

The chromatography column (Shanhai Jinhua Chromatography Equipment Factory) was Φ18 mm×400 mm, the packing specification of the DEAE Sepharose FF packing material (GE Healthcare) was Φ18 mm×235 mm, 1 CV=60 ml.

The DEAE Sepharose FF chromatography column was cleaned-in-place using 0.5M NaOH at 5 ml/min for 30 min, eluted with 3 CV of $ddH_2O$ at 5 ml/min, regenerated with 3 CV of 1M NaCl at 5 ml/min, and eluted with 3 CV of 20 mM boric acid/borax (pH 9.0, solution A) at 5 ml/min. The Q Sepharose FF purified PEG-rHuGH sample was loaded at a flow rate of 3 ml/min, eluted with 3 CV of solution A at 5 ml/min, and eluted with 6 CV of 20 mM boric acid/borax-30 mM NaCl (pH 9.0, solution B) at 5 ml/min. 20 mM boric acid/borax-100 mM NaCl (pH 9.0, solution C) was used to elute at 5 ml/min until the first and second peaks were completely detected. The eluent was detected at 280 nm (AKTA Basic100, GE Healthcare). The sample from the second peak was collected as the target sample. The buffer system of the target sample was changed to 5 mM PBNa (pH 8.5) and appropriately concentrated through ultrafiltration with 5K ultrafilter (Millipore, polyethersulfone material).

2.3 Refined Purification using Q Sepharose FF Chromatography

The chromatography column (Shanhai Jinhua Chromatography Equipment Factory) was Φ25 mm×400 mm, the packing specification of the Q Sepharose FF packing material (GE Healthcare) was Φ25 mm×200 mm, 1 CV=98 ml.

The Q Sepharose FF chromatography column was cleaned-in-place using 0.5M NaOH at 10 ml/min for 30 min, eluted with 3 CV of $ddH_2O$ at 10 ml/min, regenerated with 3 CV of 1M NaCl at 10 ml/min, and eluted with 3 CV of 5 mM PBNa (pH 8.5, solution A) at 10 ml/min. The DEAE Sepharose FF purified PEG-rHuGH sample was loaded at a flow rate of 6 ml/min, and eluted with 3 CV of solution A at 10 ml/min. 5 mM PBNa-90 mM NaCl (pH 8.5, solution B) was used to elute at 10 ml/min until the first peak was completely detected, and 5 mM PBNa-300 mM NaCl (pH 8.5, solution C) was used to elute at 10 ml/min until the second peak was completely detected. The eluent was detected at 280 nm (AKTA Basic100, GE Healthcare). The sample from the first peak was collected as the target sample. The buffer system of the target sample was changed to 3 mM NaAc/HAc-7 mM NaCl-5 mM Lys (pH 5.0) through ultrafiltration using 5K ultrafilter (Millipore, polyethersulfone material), and mannitol was supplemented to the final concentration of 45 mg/ml. The sample was sterilized through 0.2 μm filtration. A sample was taken for SDS-PAGE electrophoresis, and silver staining was used for visualization. The remaining sample was stored at −70° C. The modification product modified at pH6.0 was designated as Y6 or U6, wherein the band of higher apparent M.W. was designated as Y6-1 or U6-1, whereas the band of lower apparent M.W. was designated as Y6-2 or U6-2. The modification product at pH9.0 was designated as Y9 or U9, and the modification product at pH10.5 was designated as Y10.5 or U10.5.

Figure 4:
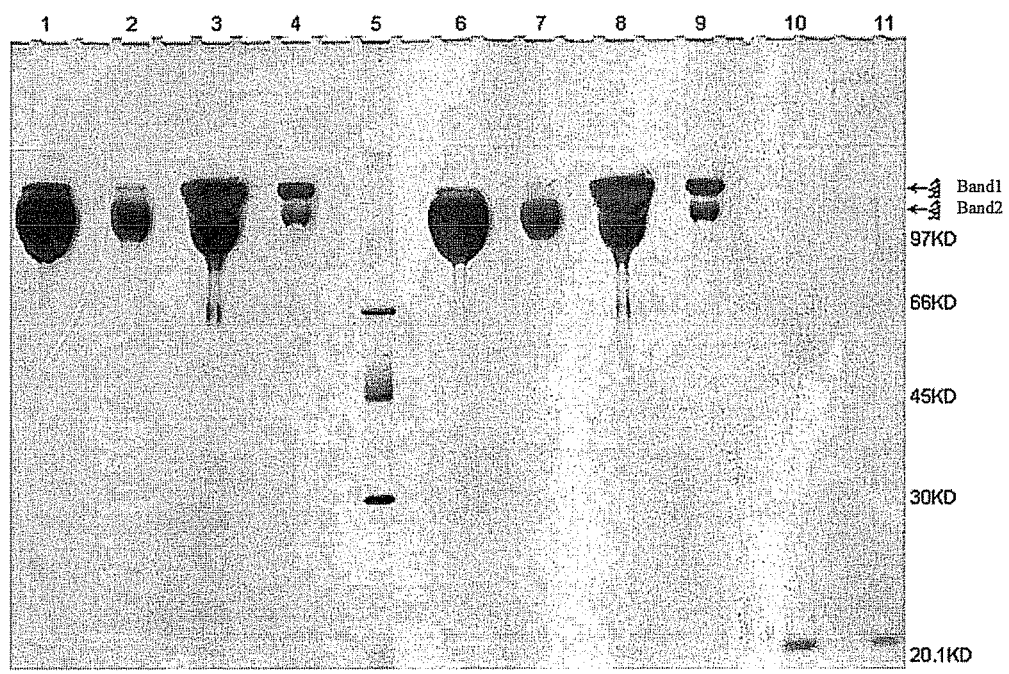
FIG. 4: The results of non-reductive SDS-PAGE of the purified rHuGH modification products modified by YPEG-NHS 40 kDa or UPEG-NHS 40 kDa at a single site at pH 6.0 or pH 10.5. The concentration of the separation gel is 12%, and silver staining is used for visualization. Lane 1: UPEG-rHuGH U10.5, loading amount 10 μg; Lane 2: UPEG-rHuGH U10.5, loading amount 2 μg; Lane 3: UPEG-rHuGH U6.0, loading amount 10 μg; Lane 4: UPEG-rHuGH U6.0, loading amount 2 μg; Lane 5: marker, LMW, GE Healthcare; Lane 6: YPEG-rHuGH Y10.5, loading amount 10 μg; Lane 7: YPEG-rHuGH Y10.5, loading amount 2 μg; Lane 8: YPEG-rHuGH Y6.0, loading amount 10 μg; Lane 9: YPEG-rHuGH Y6.0, loading amount 2 μg; Lane 10: rHuGH, loading amount 100 ng; Lane 11: rHuGH, loading amount 50 ng.

The SDS-PAGE results are shown in FIG. 4. From the electrophoresis results, the modification products at pH6.0 show clearly two bands, but the modification products at pH10.5 were mainly the band of lower apparent M.W. with a SDS-PAGE content of not lower than 80%.

3 Cellular Activity

Using GH national standard as the control, HuGH dependent rat lymphoma cell line Nb2-11 was employed to assay the cellular activity of each PEG-rHuGH sample.

Nb2-11 cells were diluted to the final concentration of $5×10^4$ cells/ml. GH national standard (lot. No.: 35-20002, 1 mg/ml/tube, 3 IU/tube; purchased from National Institute for the Control of Pharmaceutical and Biological Products) were pre-diluted to 100 ng/ml (0.0003 IU/ml), and each PEG-rHuGH sample to be assayed was pre-diluted to 0.0003 IU/ml according to the results from pre-experiments. Based on the pre-dilution, each sample was assayed after one and half times' gradient dilution. The activity of the sample was calculated according to the following equation:

$$\text{Activities of samples for examination} = \text{Activities of Standards} \times C_1/C_2 \times D_1/D_2$$

wherein: $C_1$ is the dilution folds of the sample to be assayed equivalent to half-effect amount of the standard $C_2$ is the dilution folds of the half-effect standard $D_1$ is the pre-dilution folds of the sample to be assayed $D_2$ is the pre-dilution folds of the standard Assay Method:

(1) The cells in logarithmic growth phase were taken, repeatedly pipetted, centrifuged and washed. The cells were resuspended in the diluent, and were adjusted to a concentration of $5\times10^4$ cells/ml.

(2) Each pre-diluted sample to be assayed was double gradient diluted respectively on cell plate (96-well plate, Corning), 10 gradients in total, and duplicate wells were made for each gradient, 50 μl/well. The positive control was made in 8 gradients in the same manner. The diluent was used as the negative control.

(3) Cells were added in a density of 100 μl/well, placed in $CO_2$ incubator and incubated at 37° C. for about 70 hours. ALAMARBLUE® solution (BioSource) was added at 30 μl/well, blended with shaking for 1 min. The incubation was done in $CO_2$ incubator at 37° C. for 5 hours. After shaking at room temperature for 5 min, the plate was read (wavelength of excited light 530 nm; wavelength of emission light 590 nm).

(4) Four-parameter regression method was used to plot the standard and the sample to be assayed. The titres of each sample to be assayed were calculated according to the equation of the plots of the standard and the samples to be assayed.

Figure 5:
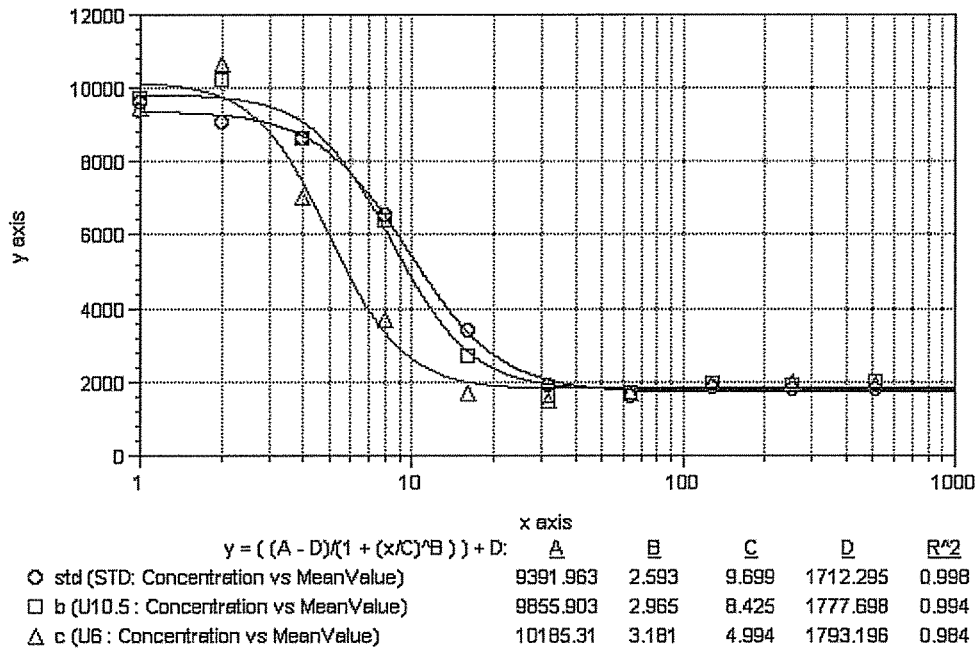
FIG. 5: The assay results of the cellular activity of the purified rHuGH modification products modified by UPEG-NHS 40 kDa at a single site at pH 6.0 or pH 10.5, duplicate plates.
Figure 5:
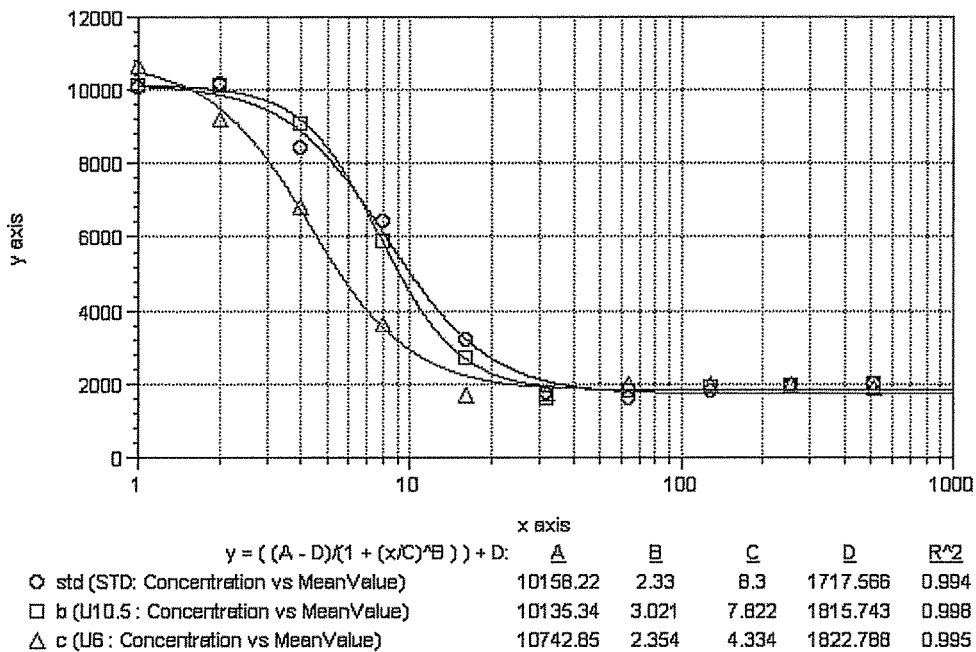
Figure 6:
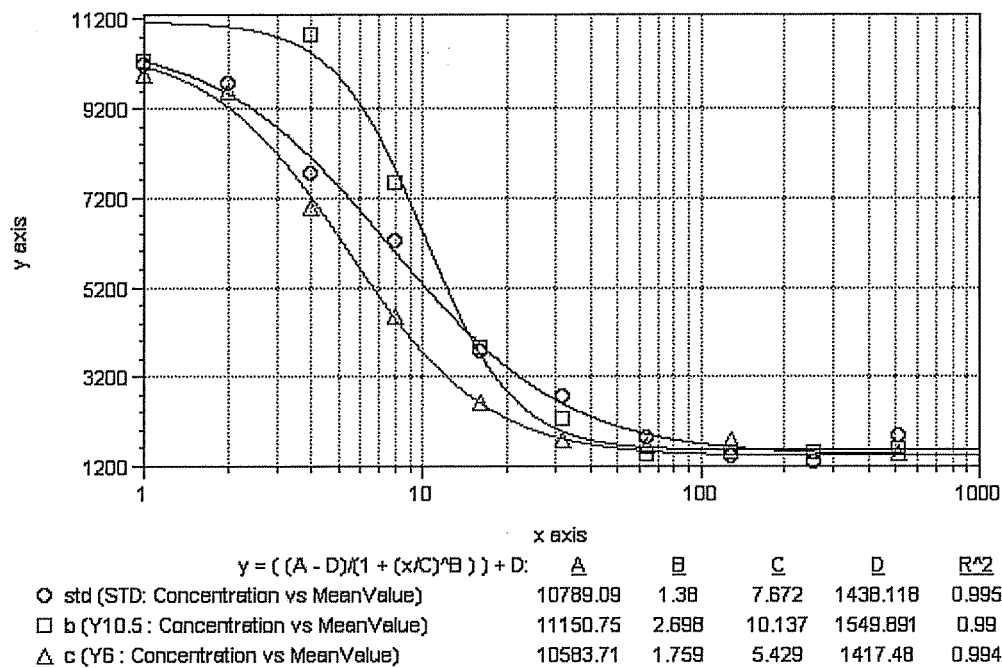
FIG. 6: The assay results of the cellular activity of the purified rHuGH modification products modified by YPEG-NHS 40 kDa at a single site at pH 6.0 or pH 10.5, duplicate plates.
Figure 6:
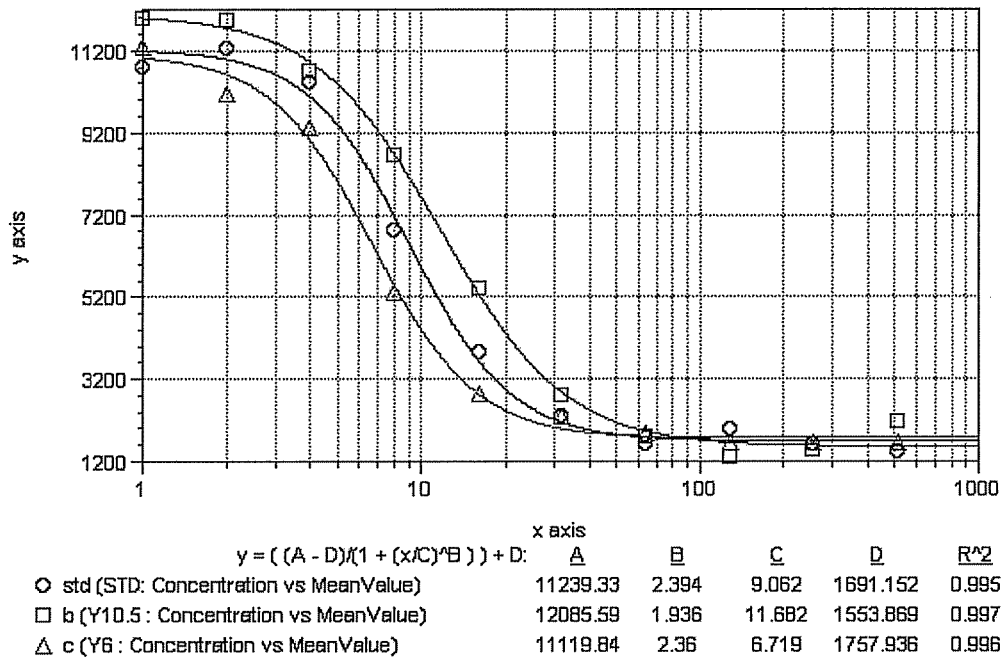

The results of the cellular activity are shown in table 2 and FIG. 5 as well FIG. 6. Duplicate samples were assayed for each sample. The cellular specific activity of YPEG-NHS modified rHuGH at pH6.0 (Y6) is $1.08\times10^{-1}$ IU/mg, the cellular specific activity of the modified product at pH9.0 (Y9) is $1.66\times10^{-1}$ IU/mg, and the cellular specific activity of the modified product at pH10.5 (Y10.5) is $2.09\times10^{-1}$ IU/mg, wherein the cellular specific activity of Y10.5 is about 2 times of that of Y6. The cellular specific activity of UPEG-NHS modified rHuGH at pH6.0 (U6) is $8.85\times10^{-2}$ IU/mg, the cellular specific activity of the modified product at pH9.0 (U9) is $1.42\times10^{-1}$ IU/mg; and the cellular specific activity of the modified product at pH10.5 (U10.5) is $1.82\times10^{-1}$ IU/mg, wherein the cellular specific activity of U10.5 is about two times of that of U6. As the pH of modification reaction increases, the cellular activity of the product modified by PEG at a single site (2 major bands) also increases correspondingly.

Figure 7:
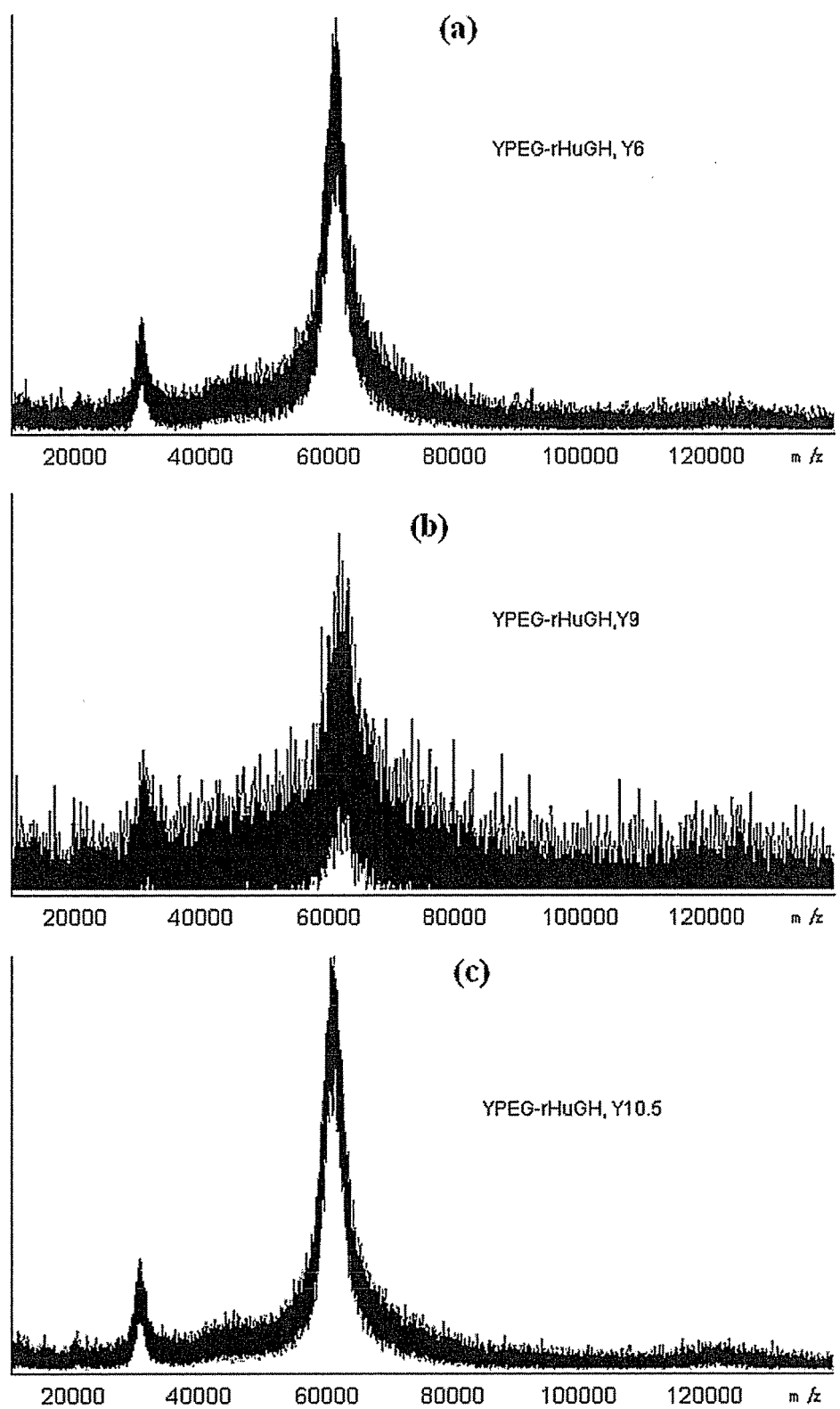
FIG. 7: The molecular weights of the purified rHuGH modification products modified by YPEG-NHS 40 kDa or UPEG-NHS 40 kDa at a single site at pH 6.0, pH 9.0 or pH 10.5, detected by MALDI-TOF MS. a: YPEG-rHuGH, Y6; b: YPEG-rHuGH, Y9; c: YPEG-rHuGH, Y10.5; d: YPEG-rHuGH, Y6-1; e: UPEG-rHuGH, U6; f: UPEG-rHuGH, U9; g: UPEG-rHuGH, U10.5; h: UPEG-rHuGH, U6-1; i: YPEG-NHS, 40 kDa; j: UPEG-NHS, 40 kDa; k: Protein Calibrate Standard II, BRUKER; l: rHuGH; m: Protein Calibrate Standard I, BRUKER.
Figure 7:
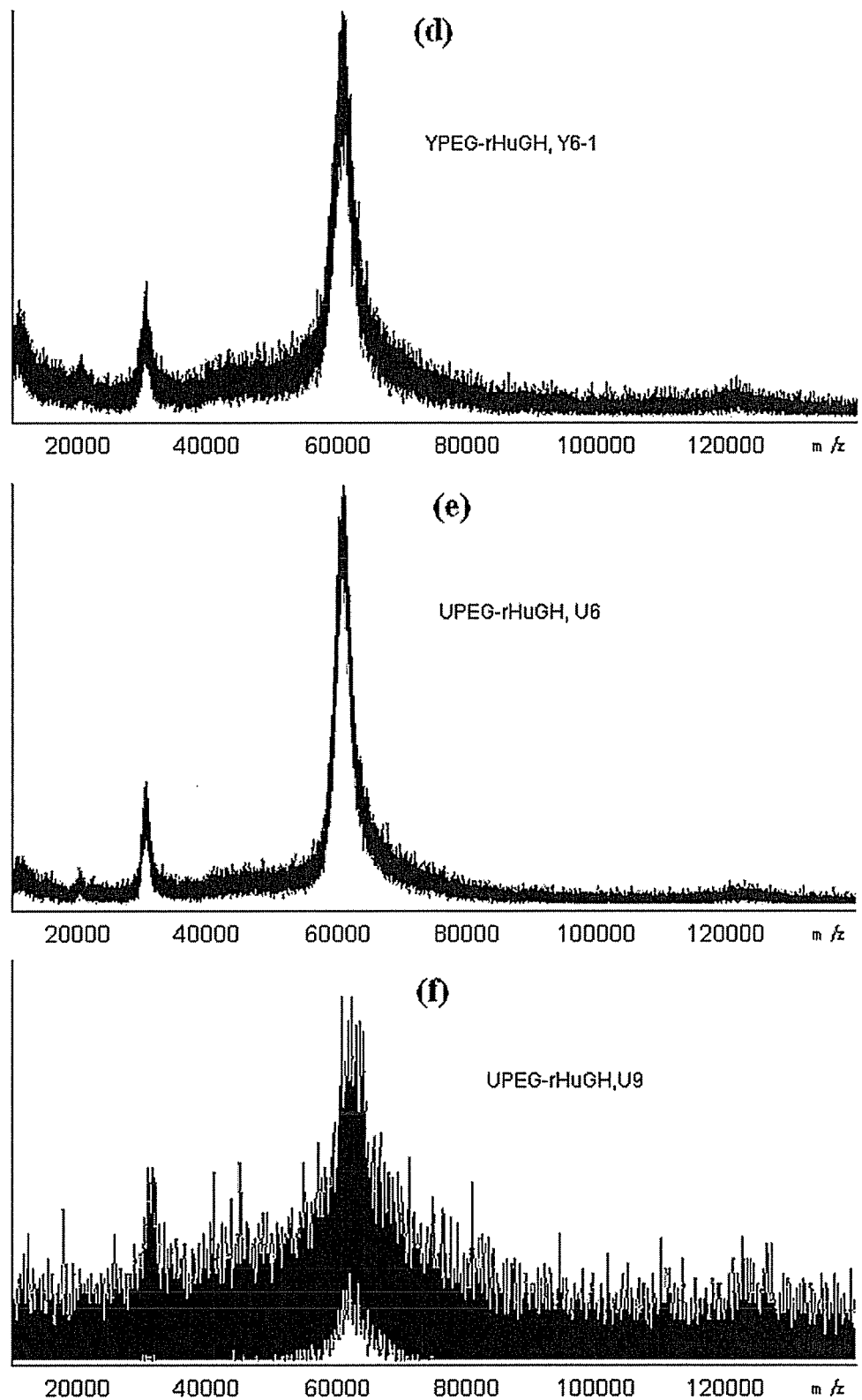
Figure 7:
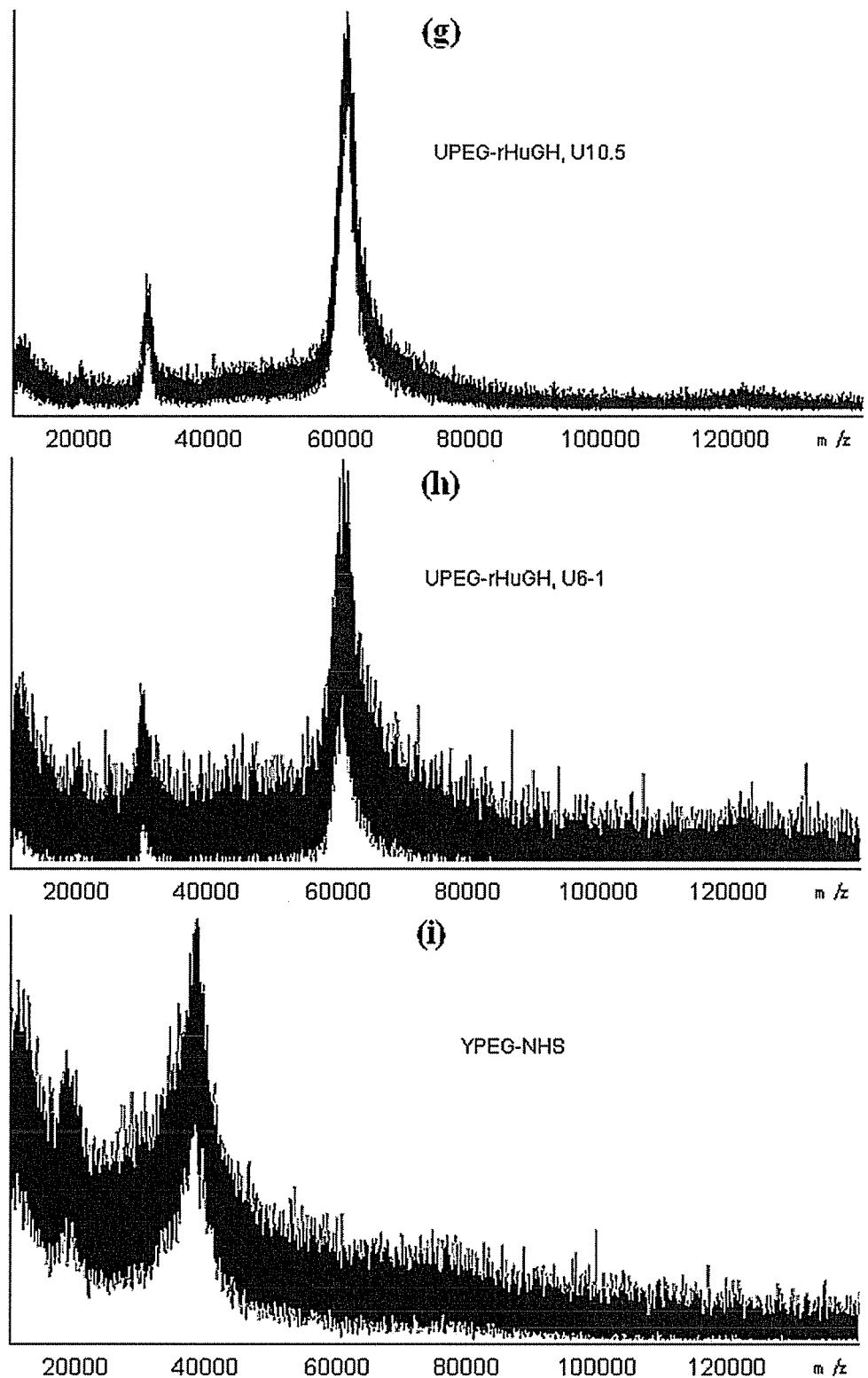
Figure 7:
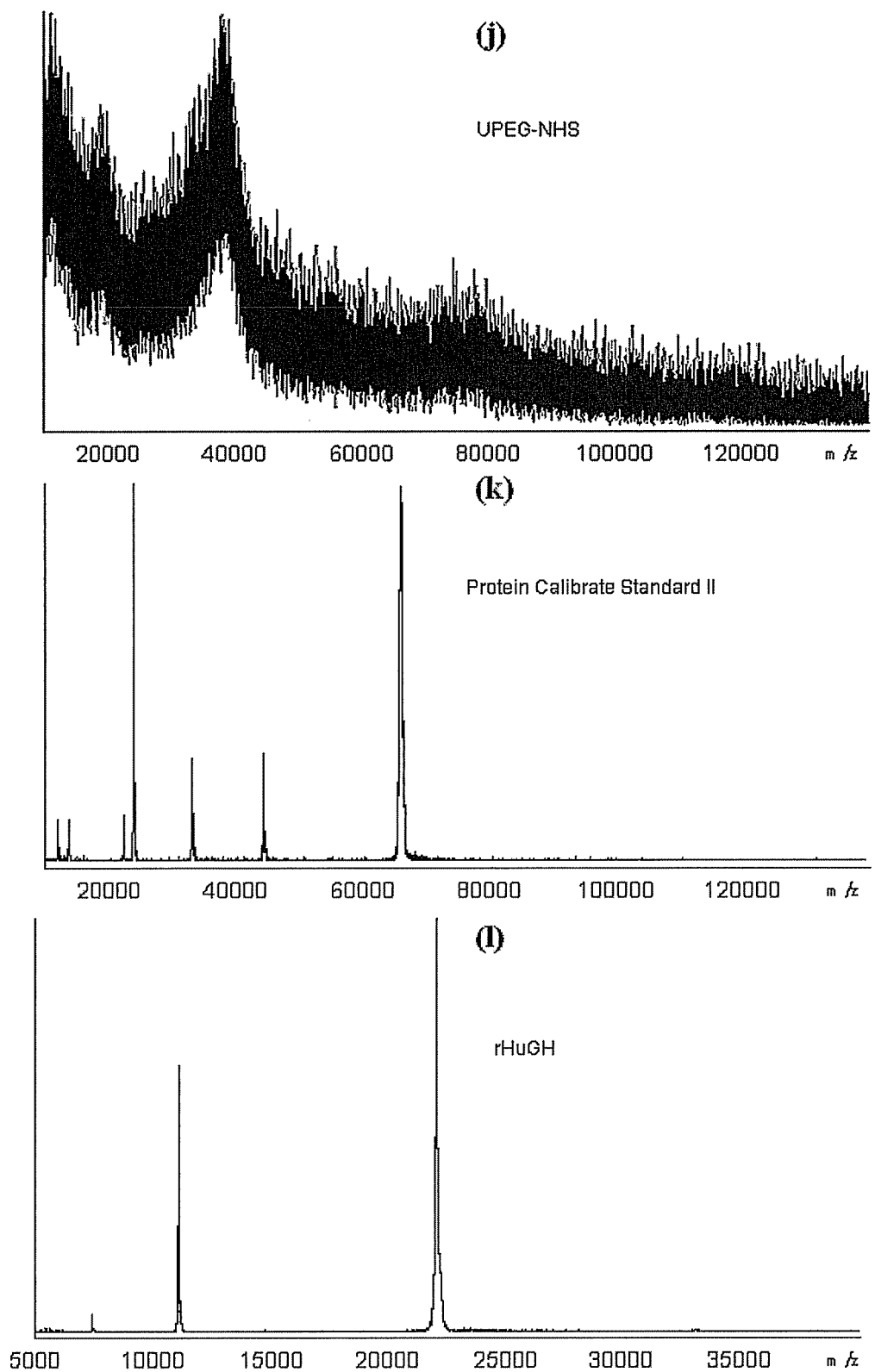
Figure 7:
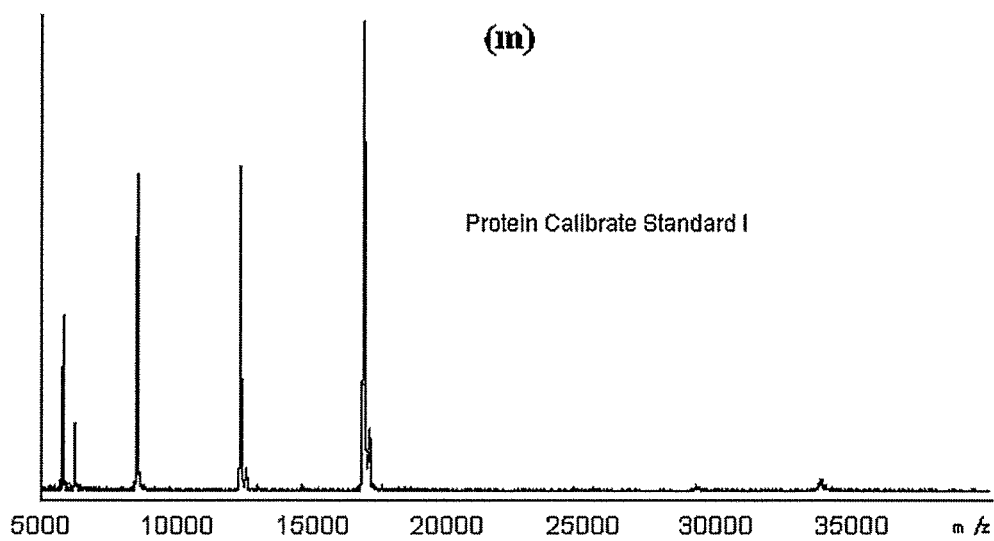

206355) and Protein Calibration Standard II (Part No. 207234) from BRUKER were used as protein molecular weight standard, and the analysis software was FLEX-ANALYSIS™ Ver.3.0.54.0. Results are shown in FIG. 7.

The YPEG-NHS modified rHuGHs at pH 6.0 (Y6), pH 9.0 (Y9) and pH 10.5 (Y10.5) all have a MS molecular weight in a range of 62012 Dalton±10%, which is consistent with the theoretical molecular weight of the rHuGH modified by YPEG at a single site (the molecular weight of YPEG-NHS is 40 kDa±10%), indicating that Y6, Y9 and Y10.5 are the rHuGH modification product modified by YPEG at a single site. The UPEG-NHS modified rHuGHs at pH 6.0 (U6), pH 9.0 (U9) and pH 10.5 (U10.5) all have a MS molecular weight in a range of 62012 Dalton±10%, which is consistent with the theoretical molecular weight of the rHuGH modification products modified by UPEG at a single site (the molecular weight of UPEG-NHS is 40 kDa±10%), indicating that U6, U9 and U10.5 are the rHuGH modification product modified by UPEG at a single site.

Example 4

The Preparation as Well the Cellular Activity and M.W. Assay of the Recombinant Human GH Modification Product of Higher Apparent Molecular Weight Modified by U-Shaped or Y-Shaped Branched PEG at a Single Site at pH6.0 (Y6-1, U6-1)

1 Modification

Two samples of 1200 mg of each UPEG-NHS and YPEG-NHS (average M.W. 40 kDa, equal-arm; lot. Nos. are ZZ004P182, ZZ004P167 respectively) (Beijing JenKem Technology Co., Ltd.) were weighted and dissolved in 12 ml of 2 mM HCl (Guangdong Guanghua Chemical Factory Co., Ltd.) respectively. 300 mg rHuGH (Xiamen Amoytop Biotech Co., Ltd.) and 10 mM PBNa (pH6.0) (Sinopharm Shanghai Chemical Reagent Co., Ltd.) were added respectively to a final total reaction volume of 60 ml. In the reaction system, the final reaction concentration of rHuGH was 5 mg/ml, the reaction molar ratio of the rHuGH to PEG-NHS was about 1:2, and the reaction pH was 6.0. Incubation was done at <10° C. for 2h with shaking, and glacial acetic acid (Shantou Xilong Chemical Co., Ltd.) was added to make pH<4.0 to stop the reaction.

TABLE 2

The cellular activity of each sample of YPEG-rHuGH and UPEG-rHuGH *

| Sample | PEG type | PEG M.W. (kDa) | Cellular specific activity ($\times10^{-1}$ IU/mg) | | |
|---|---|---|---|---|---|
| | | | Plate 1 | Plate2 | average |
| YPEG-rHuGH, Y6 | Y branched | 40 | 1.04 | 1.12 | 1.08 |
| YPEG-rHuGH, Y9 | Y branched | 40 | 1.58 | 1.74 | 1.66 |
| YPEG-rHuGH, Y10.5 | Y branched | 40 | 2.06 | 2.12 | 2.09 |
| UPEG-rHuGH, U6 | U branched | 40 | 0.88 | 0.89 | 0.88 |
| UPEG-rHuGH, U9 | U branched | 40 | 1.38 | 1.46 | 1.42 |
| UPEG-rHuGH, U10.5 | U branched | 40 | 1.84 | 1.80 | 1.82 |

Note:
* GH national standard was used as the standard. Lot. No. of the standard: 35-20002, 1 mg/ml/tube, 3 IU/tube, purchased from National Institute for the Control of Pharmaceutical and Biological Products.

4 The Molecular Weight Determined by MALDI-TOF MS

Using AUTOFLEX™ III TOF/TOF mass spectroscope (BRUKER, Germany), MALDI-TOF MS method was employed to determine the molecular weight of each sample of PEG-rHuGH. Sinapinic acid (SA, $C_{11}H_{12}O_5$, M.W. 224.22, lot number: 2006 236870 002, BRUKER) was used as the matrix, Protein Calibration Standard I (Part No.

2 The Purification of the Product of Higher Apparent Molecular Weight Modified by PEG at a Single Site (Y6-1, U6-1)

2.1 Q Sepharose FF Chromatography Purification

The rHuGH sample modified by PEG (pH 6.0) was diluted 3 times using ultrapure water, and the pH was adjusted to 9.0 using NaOH.

The chromatography column (Shanhai Jinhua Chromatography Equipment Factory) was Φ25 mm×500 mm, and the packing specification of the Q Sepharose FF packing material (GE Healthcare) was φ25 mm×310 mm, 1 CV=152 ml. The Q Sepharose FF chromatography column was cleaned-in-place using 0.5M NaOH at 10 ml/min for 30 min, eluted with 3 CV of ddH$_2$O at 10 ml/min, regenerated with 3 CV of 1M NaCl at 10 ml/min, and eluted with 5 CV of 20 mM boric acid/borax-17 mM NaCl (pH 9.0, solution A) at 10 ml/min. The ultrapure water diluted sample of the PEG modified rHuGH was loaded at a flow rate of 6 ml/min, and eluted using solution A at 10 ml/min until the first peak was completely detected. 20 mM boric acid/borax-100 mM NaCl (pH 9.0, solution B) was then used to elute at 10 ml/min until the second peak was completely detected, and 20 mM boric acid/borax-200 mM NaCl (pH 9.0, solution C) was used to elute at 10 ml/min until the third peak was completely detected. The eluent was detected at 280 nm (AKTA Basic100, GE Healthcare). The sample from the second peak was collected as the target sample. The buffer system of the target sample was changed to 5 mM NaAc/HAc (pH 4.5) through ultrafiltration with 5K ultrafilter (Millipore, polyethersulfone material).

2.2 MacroCap SP Chromatography Purification

Figure 8:
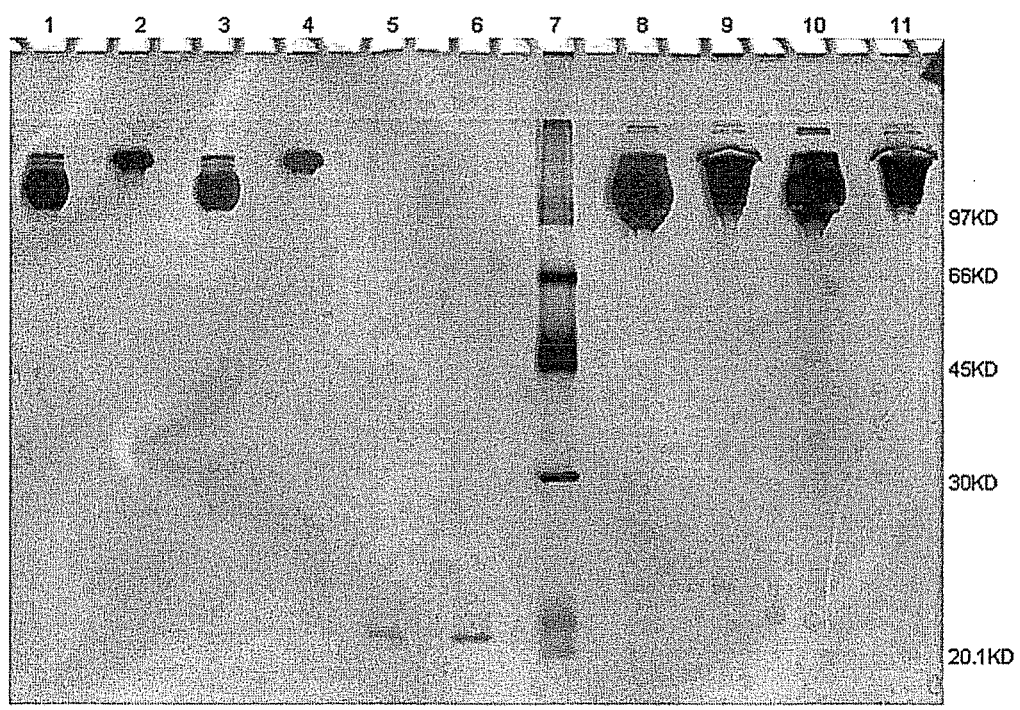
FIG. 8: The results of non-reductive SDS-PAGE of the purified rHuGH modification product of higher apparent molecular weight modified by PEG-NHS 40 kDa at a single site at pH 6.0, and of the purified rHuGH modification product modified by PEG-NHS 40 kDa at a single site at pH 10.5. The concentration of the separation gel is 12%, and silver staining is used for visualization. Lane 1: YPEG-rHuGH Y10.5, loading amount 2 μg; Lane 2: YPEG-rHuGH Y6.0-1, loading amount 2 μg; Lane 3: UPEG-rHuGH U10.5, loading amount 2 μg; Lane 4: UPEG-rHuGH U6.0-1, loading amount 2 μg; Lane 5: rHuGH, loading amount 50 ng; Lane 6: rHuGH, loading amount 100 ng; Lane 7: marker, LMW, GE Healthcare; Lane 8: YPEG-rHuGH Y10.5, loading amount 10 μg; Lane 9: YPEG-rHuGH Y6.0-1, loading amount 10 μg; Lane 10: UPEG-rHuGH U10.5, loading amount 10 μg; Lane 11: UPEG-rHuGH U6.0-1, loading amount 10 μg.
Figure 9:
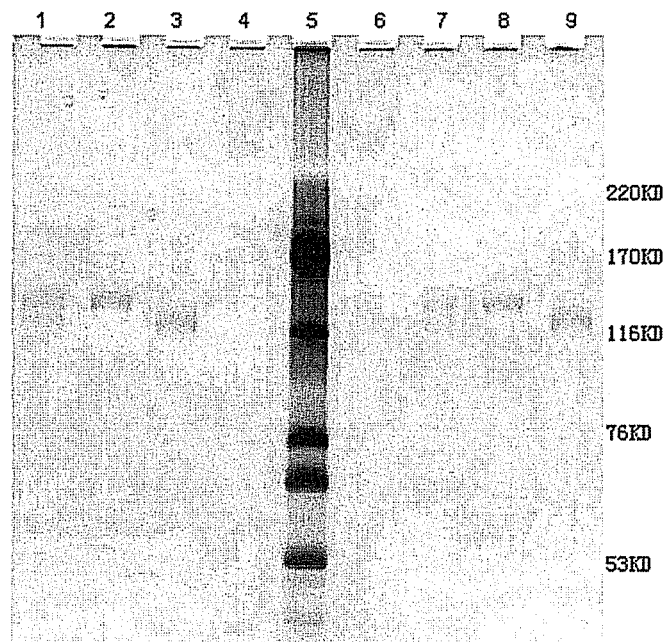
FIG. 9: The apparent molecular weights detected by non-reductive SDS-PAGE of the purified rHuGH modification products (Y6-1, U6-1) of higher apparent molecular weight modified by PEG-NHS 40 kDa at a single site at pH 6.0, and of the purified rHuGH modification products (Y10.5, U10.5) modified by PEG-NHS 40 kDa at a single site at pH 10.5. Lane 1: YPEG-rHuGH Y6-1+YPEG-rHuGH Y10.5, each 25 ng; Lane 2: YPEG-rHuGH Y6-1, 50 ng; Lane 3: YPEG-rHuGH Y10.5, 50 ng; Lane 4, 6: blank; Lane 5: marker, HMW, GE Healthcare; Lane 7: UPEG-rHuGH U6-1+UPEG-rHuGH U10.5, each 25 ng; Lane 8: UPEG-rHuGH U6-1, 50 ng; Lane 9: UPEG-rHuGH U10.5, 50 ng.

The chromatography column (Shanhai Jinhua Chromatography Equipment Factory) was Φ12 mm×300 mm, and the packing specification of MacroCap SP packing material (GE Healthcare) was Φ12 mm×180 mm, 1 CV=20 ml. The MacroCap SP chromatography column was cleaned-in-place using 0.5M NaOH at 1 ml/min for 30 min, eluted with 3 CV of ddH$_2$O at 1 ml/min, regenerated with 3 CV of 1M NaCl at 1 ml/min, and eluted with 5 CV of 5 mM NaAc/HAc (pH 4.5, solution A) at 1 ml/min. The Q Sepharose FF purified PEG-rHuGH sample was loaded at a flow rate of 1 ml/min, and eluted with 3 CV of solution A at 1 ml/min. 5 mM NaAc/HAc-100 mM NaCl (pH 4.5, solution B) was used to elute with 5 CV in a gradient of 0%-30% solution B at 1 ml/min, eluted with 10 CV in a gradient of 30%-45% B, and then eluted with 5 mM NaAc/HAc-1M NaCl (pH 4.5, solution C) at 1 ml/min until the first and the second peaks were completely detected. The eluent was detected at 280 nm (AKTA Basic100, GE Healthcare). The eluent between the fifth and the eighth CV during the elution with a gradient of 30%-45% solution B was collected as the target sample. The buffer system of the target sample was changed to 3 mM NaAc/HAc-7 mM NaCl-5 mM Lys (pH 5.0) through ultrafiltration with 5K ultrafilter (Millipore, polyethersulfone material), and mannitol was supplemented to a final concentration of 45 mg/ml. The sample was sterilized through 0.2 μm filtration. A sample was taken for SDS-PAGE electrophoresis, and silver staining was used for visualization. The remaining sample was stored at −70° C. The sample numbers were: U6-1, Y6-1. The results of the SDS-PAGE electrophoresis are shown in FIG. 8, and the apparent molecular weight results of the SDS-PAGE electrophoresis are shown in FIG. 9.

In the case of loading 10 μg PEG-rHuGH sample, a small amount of the product modified at more than one site was detected in each sample of PEG-rHuGH, and the content of the substrate protein (rHuGH) in each sample was not more than 0.5% (FIG. 8), wherein the content of the major band is not lower than 80%. The apparent molecular weight of each PEG-rHuGH sample determined by the SDS-PAGE electrophoresis shows one major band, wherein the apparent molecular weight of Y6-1 is clearly higher than that of Y10.5, and the apparent molecular weight of U6-1 is clearly higher than that of U10.5 (FIG. 9).

3 The Molecular Weight Detected by MALDI-TOF MS

Using AUTOFLEX™ TOF/TOF mass spectroscope (BRUKER, Germany), MALDI-TOF MS method was used to assay the molecular weight of each PEG-rHuGH sample. The detection method was the same as that in Example 3. The results are shown in FIG. 7.

The MS molecular weights of Y6-1 and U6-1 are both in a range of 62012 Dalton±10%, which is consistent with the theoretical molecular weight of the rHuGH modified by PEG at a single site (the molecular weights of YPEG-NHS and UPEG-NHS are 40 kDa±10%), indicating that both are the products modified by PEG at a single site.

Using GH national standard as the control, HuGH dependent rat lymphoma cell line Nb2-11 was used to assay the cellular activity of each PEG-rHuGH sample, comparing the cellular activity difference between Y6-1 and Y10.5, U6-1 and U10.5. The assay method was the same as that in Example 3. The results are shown in table 3, triplicate for each sample.

The average cellular specific activity of Y10.5 is 2.08× $10^{-1}$ IU/mg, the average cellular specific activity of Y6-1 is 5.50×$10^{-2}$ IU/mg; the average cellular specific activity of U10.5 is 2.28×$10^{-1}$ IU/mg, and the average cellular specific activity of U6-1 is 5.00×$10^{-2}$ IU/mg. The average cellular specific activity of Y10.5/U10.5 is clearly higher than that of Y6-1/U6-1, and can reach up to 3 times of the latter.

TABLE 3

The cellular activity of each YPEG-rHuGH or UPEG-rHuGH sample[1]

| Sample | PEG type | PEG M.W. (kDa) | Number of PEG modification sites | Cellular specific activity (×$10^{-1}$ IU/mg)[2] |
|---|---|---|---|---|
| YPEG-rHuGH, Y10.5 | Y branched | 40 | single | 2.08 ± 0.10 |
| YPEG-rHuGH, Y6-1 | Y branched | 40 | single | 0.55 ± 0.06 |
| UPEG-rHuGH, U10.5 | U branched | 40 | single | 2.28 ± 0.14 |
| UPEG-rHuGH, U6-1 | U branched | 40 | single | 0.50 ± 0.06 |

Note:
[1] using GH national standard as the standard. Lot. No. of the standard: 35-20002, 1 mg/ml/tube, 3 IU/tube, purchased from National Institute for the Control of Pharmaceutical and Biological Products.
[2] average of triplicate samples.

Example 5

The In Vivo Biological Activity Assay of YPEG-rHuGH (Y10.5) and UPEG-rHuGH (U10.5)

Using rats with the pituitary glands removed as animal models, the in vivo animal growth promoting biological activity of YPEG-rHuGH (Y10.5) and UPEG-rHuGH (U10.5) were assayed according to the growth hormone bioassay as described in *Pharmacopoeia of the People's Republic of China*, version 2005, Volume 3, Appendix XII P, i.e. observing the effect on the growth and development of rats with the pituitary glands removed (no endogenous GH) one week after a single administration.

Wistar rats, SPF level, male, born 26-28d, body weight of 60-80 g, provided by the experiment animal center of National Institute for the Control of Pharmaceutical and Biological Products (animal certification No.: SCXK (Jing) 2005-0004), were used. 2-3 weeks before the experiment, the pituitary glands of rats were removed aseptically by surgery, and the rats were then normally raised in a S-2 laboratory to recover for further experiment. The qualified rats with pituitary glands removed were selected, and divided evenly into 10 groups of 10 rats according to body weight, specifically: negative control (blank solvent) group; positive control rHuGH (GH national standard, prepared by National Institute for the Control of Pharmaceutical and Biological Product, 3 IU·mg$^{-1}$·tube$^{-1}$), low dose (2.7 IU·kg$^{-1}$), medium dose (5.3 IU·kg$^{-1}$) and high dose (10.7 IU·kg$^{-1}$) groups, administered in 6 times, once per day, 6 consecutive administrations; low dose (2.7 IU·kg$^{-1}$), medium dose (5.3 IU·kg$^{-1}$) and high dose (10.7 IU·kg$^{-1}$) groups of the testing sample Y10.5, low dose (2.7 IU·kg$^{-1}$), medium dose (5.3 IU·kg$^{-1}$) and high dose (10.7 IU·kg$^{-1}$) groups of the testing sample U10.5, single administration once in the first day when the standard was administered. Y10.5 and U10.5 were formulated according to the estimated titre of 3 IU/mg. Administration was performed by subcutaneous injection of 0.5 ml to the neck of the animal. The negative control group was only administered the solvent, once per day, 6 times in total. The rats were sacrificed 24 h after the last administration in the positive control group, and the body weights and the width of tibial growth plates were measured. The data were processed according to the growth hormone assay in Appendix XII P and the statistic method for biological assay in Appendix XIV of the *Pharmacopoeia of the People's Republic of China*, version 2005.

The biological titre of YPEG-rHuGH (Y10.5) is 5.0 IU·mg$^{-1}$, the biological titre of UPEG-rHuGH (U10.5) is 5.2 IU·mg$^{-1}$, both more than 1.5 times of the normal rHuGH. Single administration of YPEG-rHuGH (Y10.5) or UPEG-rHuGH (U10.5) has a higher biological activity for promoting the body growth in animal and a longer pharmaceutical effect than the sum of daily injected rHuGH.

Example 6

Figure 10:
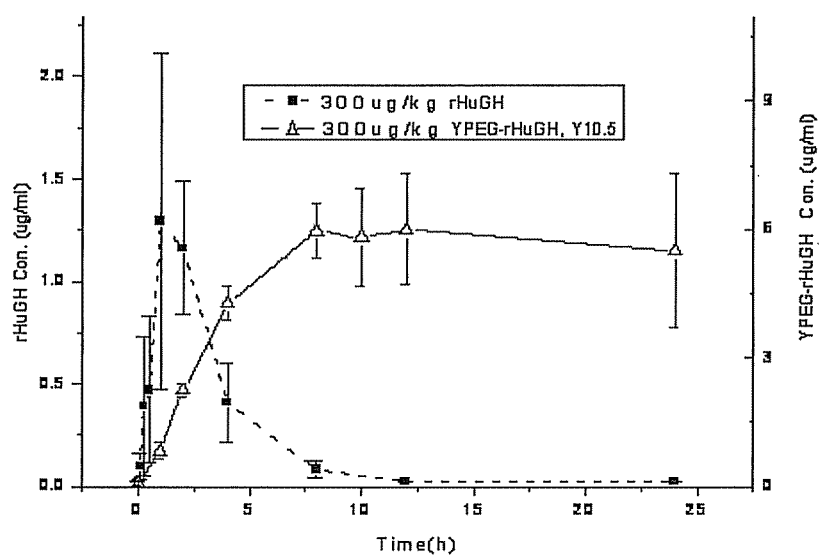
FIG. 10: The curve of average serum drug concentration vs. time of single subcutaneous injection in crab-eating macaque of 300 μg·kg$^{-1}$ of rHuGH and YPEG-rHuGH (Y10.5) respectively.

The Serum Drug Metabolic Half-Life of YPEG-rHuGH (Y10.5) in Crab-Eating Macaque 6 crab-eating macaques were selected, 3 female and 3 male, body weight of 3.24-5.48 kg (Guangxi Beihai Yu Qi Experiment Animal technology co. Ltd., certification No.: SCXK (Gui)2005-0005). The experiment included two groups of 3 crab-eating macaques: one group with subcutaneous injection of YPEG-rHuGH (Y10.5) at 300 µg·kg$^{-1}$ (2♂, 1♀) and the other group with subcutaneous injection of rHuGH (Saizen, Laboratoires Serono S.A. Switzerland) at 300 µg·kg$^{-1}$ (1♂, 2♀), single administration. After administration, the venous blood was taken regularly from the hind leg opposite to the injected side, and the serum was separated. Human Growth Hormone ELISA kit from R&D was used to assay the blood drug concentration through ELISA, and the curve of blood drug concentration was plotted to calculate drug metabolic half-life. The results are shown in FIG. 10.

After subcutaneous injection of YPEG-rHuGH (Y10.5) at 300 µg·kg$^{-1}$ in crab-eating macaques, the time-to-peak of drug concentration in serum is 8-24 h. The drug was eliminated slowly. The average drug metabolic half-life in serum is 41.33 h. After subcutaneous injection of rHuGH (Saizen) at 300 µg·kg$^{-1}$ in crab-eating macaques, the time-to-peak of drug concentration in serum is 1-2 h, and by 24 h the concentration decreases to the level before administration. The elimination is clearly faster than YPEG-rHuGH (Y10.5). The average drug metabolic half-life in serum is 1.80 h. The average drug metabolic half-life in serum of YPEG-rHuGH (Y10.5) is more than 20 times of rHuGH.

What is claimed is:

1. A method for preparing a PEGylated growth hormone preparation, the method comprising:
   a) bringing U-shaped or Y-shaped branched double-stranded PEG into contact with a growth hormone in a solution with a pH not lower than 8.0 to produce a product modified by the double-stranded PEG at a single site;
   b) assaying the product modified by the double-stranded PEG at a single site obtained in step a) by sodium dodecyl sulfate-polyacrylamide gel electrophoresis (SDS-PAGE) of an appropriate concentration, wherein the product shows two bands; and
   c) separating and recovering the product modified by the double-stranded PEG at a single site;
   wherein the recovered product is a mixture predominantly containing the product of lower apparent molecular weight modified by the double-stranded PEG at a single site, wherein the SDS-PAGE content of the product of lower apparent molecular weight modified by the double-stranded PEG at a single site is not lower than 70%.

2. The method of claim 1, wherein the double-stranded PEG is Y-shaped branched PEG of the following structural formula (I),

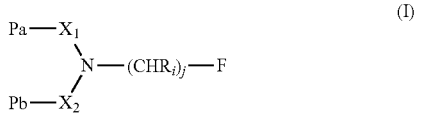

wherein, $P_a$ and $P_b$ are same or different PEG; j is an integer from 1 to 12; $R_i$ is H, substituted or unsubstituted $C_{1-12}$ alkyl, substituted aryl, aralkyl, or heteroalkyl; $X_1$ and $X_2$ are independently linking group, wherein $X_1$ is $(CH_2)_n$, $X_2$ is selected from the group consisting of: $(CH_2)n$, $(CH_2)_nOCO$, $(CH_2)_nNHCO$, $(CH_2)_nCO$, wherein n is an integer from 1 to 10; F is a terminal group selected from the group consisting of: hydroxyl, carboxyl, ester group, acyl chloride, hydrazide, maleimide, pyridine disulfide, capable of reacting with an amino, hydroxyl or hydrosulfide group of a therapeutic agent or substrate to form a covalent bond.

3. The method of claim 2, wherein the Y-shaped branched PEG is of the following structural formula (II):

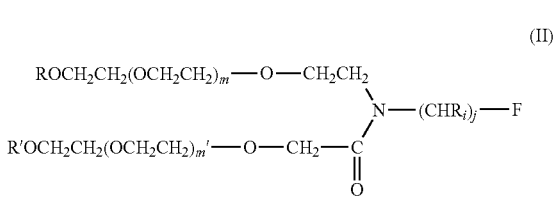

wherein R and R' are independently low molecular weight alkyl and m and m' denote the degree of polymerization and can be any integer.

4. The method of claim 3, wherein the Y-shaped branched PEG is of the following structural formula (III):

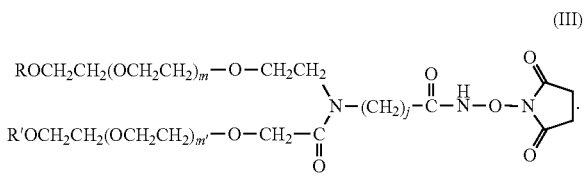

5. The method of claim 1, wherein the double stranded PEG is U-shaped branched PEG of the following structural formula (IV),

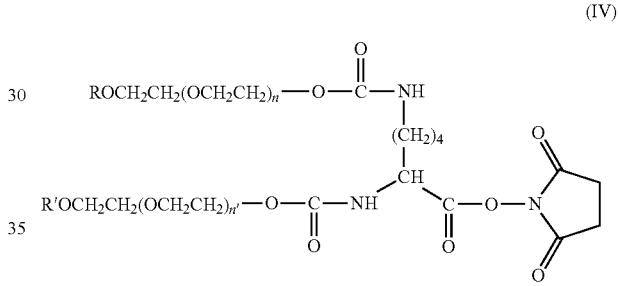

wherein, R and R' are independently low molecular weight alkyl; n and n' denote the degree of polymerization and can be any integer; n+n' is from 600 to 1500; the average molecular weight of the U-shaped branched PEG is about from 26 kiloDaltons (kDa) to 66 kDa.

6. A method for preparing a PEGylated growth hormone preparation, comprising the following steps:
   a) in a solution having a pH of 9.0 or 10.5, bringing a double-stranded PEG of the following structural formula (III) into contact with human growth hormone, wherein the molar ratio of the growth hormone to the double stranded PEG is about 1:2;

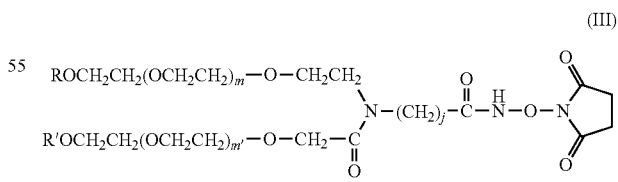

wherein m+m' is 910, the average total molecular weight of the PEG is about 40 kDa;
   b) assaying the product modified by the double-stranded PEG at a single site obtained in step a) in 12% SDS-PAGE;
   c) separating and recovering the product modified by the double-stranded PEG at a single site using gel chromatography selected from Q Sepharose FF chromatography, DEAE Sepharose FF chromatography or MacroCap SP chromatography, wherein the SDS-PAGE content of the product of lower apparent molecular weight in the recovered product modified by the double-stranded PEG at a single site is not lower than 70%.

7. A PEGylated growth hormone preparation prepared according to the method of claim 1, wherein the growth hormone is extracted from a natural source or obtained by recombinant biotechnology, and further wherein at least 70% of the PEGylated growth hormone preparation comprises a growth hormone polypeptide modified with a double-stranded PEG moiety linked to an ε-NH$_2$ group of a single Lys residue present within the growth hormone polypeptide.

8. The PEGylated growth hormone preparation of claim 7, wherein the product modified by the PEG at a single site is shown as the following formula (VII):

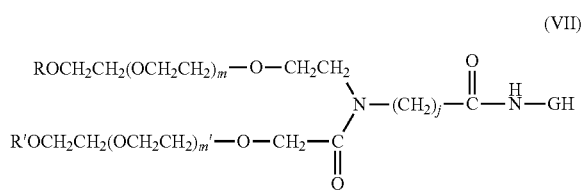

(VII)

wherein, R and R' are independently low molecular weight alkyl, m+m' is 910;
and j is an integer from 1 to 12.

9. A method for treating a patient with a disease in need of growth hormone treatment comprising administering a therapeutically effective amount of the PEGylated growth hormone preparation of claim 7 to the patient.

10. The PEGylated growth hormone preparation of claim 7, wherein the recombinant growth hormone is artificially synthesized or expressed by an expression system selected from the group consisting of a prokaryotic system; a eukaryotic system; an insect cell system; and a mammalian cell system.

11. The PEGylated growth hormone preparation of claim 8, wherein the recombinant growth hormone is artificially synthesized or expressed by an expression system selected from the group consisting of a prokaryotic system; a eukaryotic system; an insect cell system; and a mammalian cell system.

12. A composition comprising a pharmaceutically effective amount of the PEGylated growth hormone preparation of claim 7 and a pharmaceutically acceptable carrier or excipient.

13. A composition comprising a pharmaceutically effective amount of the PEGylated growth hormone preparation of claim 8 and a pharmaceutically acceptable carrier or excipient.

14. A method for treating a patient with a disease in need of growth hormone treatment comprising administering a therapeutically effective amount of the PEGylated growth hormone preparation of claim 8 to the patient.

15. A composition comprising a pharmaceutically effective amount of the PEGylated growth hormone preparation of claim 10 and a pharmaceutically acceptable carrier or excipient.

16. A composition comprising a pharmaceutically effective amount of the PEGylated growth hormone preparation of claim 11 and a pharmaceutically acceptable carrier or excipient.

17. A method for treating a patient with a disease in need of growth hormone treatment comprising administering a therapeutically effective amount of the composition of claim 12 to the patient.

18. A method for treating a patient with a disease in need of growth hormone treatment comprising administering a therapeutically effective amount of the composition of claim 13 to the patient.

19. A method for treating a patient with a disease in need of growth hormone treatment comprising administering a therapeutically effective amount of the composition of claim 15 to the patient.

20. A method for treating a patient with a disease in need of growth hormone treatment comprising administering a therapeutically effective amount of the composition of claim 16 to the patient.

21. The PEGylated growth hormone preparation of claim 7, wherein the growth hormone comprises an amino acid sequence comprising SEQ ID NO: 1.

22. The PEGylated growth hormone preparation of claim 8, wherein R and R' are independently $C_1$-$C_4$ alkyl.

23. The PEGylated growth hormone preparation of claim 8, wherein R or R' is methyl.

24. The PEGylated growth hormone preparation of claim 7, wherein at least 80% of the PEGylated growth hormone preparation comprises a growth hormone polypeptide modified with a double-stranded PEG moiety linked to an ε-NH$_2$ group of a single Lys residue present within the growth hormone polypeptide.

25. The PEGylated growth hormone preparation of claim 7, wherein at least 90% of the PEGylated growth hormone preparation comprises a growth hormone polypeptide modified with a double-stranded PEG moiety linked to an ε-NH$_2$ group of a single Lys residue present within the growth hormone polypeptide.

26. The PEGylated growth hormone preparation of claim 10, wherein the prokaryotic system is *E. coli*.

27. The PEGylated growth hormone preparation of claim 10, wherein the eukaryotic system is *Pichia*.

28. The PEGylated growth hormone preparation of claim 10, wherein the mammalian cell system is CHO cell.

29. The PEGylated growth hormone preparation of claim 11, wherein the prokaryotic system is *E. coli*.

30. The PEGylated growth hormone preparation of claim 11, wherein the eukaryotic system is *Pichia*.

31. The PEGylated growth hormone preparation of claim 11, wherein the mammalian cell system is CHO cell.

32. The composition of claim 12, wherein the pharmaceutically acceptable carrier or excipient comprises one or more of mannitol, an amino acid, sodium chloride, acetic acid, and sodium acetate.

33. The composition of claim 13, wherein the pharmaceutically acceptable carrier or excipient comprises one or more of mannitol, an amino acid, sodium chloride, acetic acid, and sodium acetate.

34. The composition of claim 15, wherein the pharmaceutically acceptable carrier or excipient comprises one or more of mannitol, an amino acid, sodium chloride, acetic acid, and sodium acetate.

35. The composition of claim 16, wherein the pharmaceutically acceptable carrier or excipient comprises one or more of mannitol, an amino acid, sodium chloride, acetic acid and sodium acetate.

36. The method of claim 1, wherein the solution has a pH of not lower than 9.0.

37. The method of claim 36, wherein the solution has a pH of not lower than 9.5.

38. The method of claim 37, wherein the solution has a pH of not lower than 10.0.

39. The method of claim 38, wherein the solution has a pH of not lower than 10.5.

40. The method of claim 1, wherein the growth hormone is human growth hormone.

41. The method of claim 1, wherein the growth hormone is present in a ratio of 1:2 with respect to the double stranded PEG.

42. The method of claim 1, wherein the SDS-PAGE content of the product of lower apparent molecular weight modified by the double-stranded PEG at a single site is not lower than 80%.

43. The method of claim 42, wherein the SDS-PAGE content of the product of lower apparent molecular weight modified by the double-stranded PEG at a single site is not lower than 90%.

44. The method of claim 1, further comprising a purification step subsequent to the separating and recovering step.

45. The method of claim 44, wherein the purification step employs gel chromatography.

46. The method of claim 3, wherein R and R' are independently $C_1$-$C_4$ alkyl.

47. The method of claim 46, wherein R and R' are independently methyl.

48. The method of claim 3, wherein m+m' is from 600 to 1500.

49. The method of claim 48, wherein m+m' is 910.

50. The method of claim 4, wherein the Y-shaped branched PEG has an average molecule weight of about 26 kilodaltons (kDa) to 60 kDa.

51. The method of claim 50, wherein the Y-shaped branched PEG has an average molecule weight of about 40 kDa.

52. The method of claim 4, wherein the Y-shaped branched PEG is of equal-arm.

53. The method of claim 5, wherein R and R' are independently $C_1$-$C_4$ alkyl.

54. The method of claim 5, wherein n+n' is 910.

55. The method of claim 5, wherein the U-shaped branched PEG has an average molecule weight of about 40 kDa.

56. The method of claim 5, wherein the U-shaped branched PEG is of equal-arm.

57. The method of claim 6, wherein the SDS-PAGE content of the product of lower apparent molecular weight in the recovered product modified by the double-stranded PEG at a single site is not lower than 80%.

58. The method of claim 57, wherein the SDS-PAGE content of the product of lower apparent molecular weight in the recovered product modified by the double-stranded PEG at a single site is not lower than 90%.

59. The method of claim 9, wherein the disease in need of growth hormone treatment is selected from the group consisting of dwarfism, burn, wound, bone fracture, bleeding ulcer, renal failure, acquired immunodeficiency syndrome (AIDS), endogenous growth hormone deficiency dwarfism, Turner syndrome, anabolic disorder, and adult growth hormone deficiency.

60. The method of claim 14, wherein the disease in need of growth hormone treatment is selected from the group consisting of dwarfism, burn, wound, bone fracture, bleeding ulcer, renal failure, acquired immunodeficiency syndrome (AIDS), endogenous growth hormone deficiency dwarfism, Turner syndrome, anabolic disorder, and adult growth hormone deficiency.

61. The method of claim 17, wherein the disease in need of growth hormone treatment is selected from the group consisting of dwarfism, burn, wound, bone fracture, bleeding ulcer, renal failure, acquired immunodeficiency syndrome (AIDS), endogenous growth hormone deficiency dwarfism, Turner syndrome, anabolic disorder, and adult growth hormone deficiency.

62. The method of claim 37, wherein the disease in need of growth hormone treatment is selected from the group consisting of dwarfism, burn, wound, bone fracture, bleeding ulcer, renal failure, acquired immunodeficiency syndrome (AIDS), endogenous growth hormone deficiency dwarfism, Turner syndrome, anabolic disorder, and adult growth hormone deficiency.

63. The method of claim 19, wherein the disease in need of growth hormone treatment is selected from the group consisting of dwarfism, burn, wound, bone fracture, bleeding ulcer, renal failure, acquired immunodeficiency syndrome (AIDS), endogenous growth hormone deficiency dwarfism, Turner syndrome, anabolic disorder, and adult growth hormone deficiency.

64. The method of claim 20, wherein the disease in need of growth hormone treatment is selected from the group consisting of dwarfism, burn, wound, bone fracture, bleeding ulcer, renal failure, acquired immunodeficiency syndrome (AIDS), endogenous growth hormone deficiency dwarfism, Turner syndrome, anabolic disorder, and adult growth hormone deficiency.

* * * * *

```
SEQUENCE LISTING

<160> NUMBER OF SEQ ID NOS: 1

<210> SEQ ID NO 1
<211> LENGTH: 191
<212> TYPE: PRT
<213> ORGANISM: Homo sapiens

<400> SEQUENCE: 1

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160
```

```
Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```